(12) United States Patent
Herron et al.

(10) Patent No.: US 7,090,929 B2
(45) Date of Patent: Aug. 15, 2006

(54) METALLIC COMPLEXES COVALENTLY BOUND TO CONJUGATED POLYMERS AND ELECTRONIC DEVICES CONTAINING SUCH COMPOSITIONS

(75) Inventors: Norman Herron, Newark, DE (US); Howard E. Simmons, III, Wilmington, DE (US); Daniel David Lecloux, Buellton, CA (US); Frank P. Uckert, Santa Barbara, CA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 18 days.

(21) Appl. No.: 10/625,096

(22) Filed: Jul. 22, 2003

(65) Prior Publication Data

US 2004/0072018 A1 Apr. 15, 2004

Related U.S. Application Data

(60) Provisional application No. 60/399,934, filed on Jul. 30, 2002.

(51) Int. Cl.
*H05B 33/14* (2006.01)
*H01L 51/50* (2006.01)
*H01L 27/32* (2006.01)
*H01L 51/52* (2006.01)
*H01L 51/54* (2006.01)

(52) U.S. Cl. .............. 428/690; 428/917; 313/504; 313/506; 257/89; 252/301.16

(58) Field of Classification Search .......... 428/690, 428/917; 313/504, 506; 257/40, 88, 89; 252/301.16

See application file for complete search history.

(56) References Cited

U.S. PATENT DOCUMENTS

| 5,247,190 | A | 9/1993 | Friend et al. |
| 5,408,109 | A | 4/1995 | Heeger et al. |
| 5,442,021 | A | 8/1995 | Heiliger |
| 5,552,678 | A | 9/1996 | Tang et al. |
| 5,653,914 | A | 8/1997 | Holmes et al. |
| 6,303,238 | B1 | 10/2001 | Thompson et al. |
| 2001/0015432 | A1 | 8/2001 | Igarashi |
| 2002/0028347 | A1 | 3/2002 | Marrocco, III et al. |
| 2002/0193532 | A1* | 12/2002 | Ikehira et al. ............ 525/333.3 |
| 2003/0091862 | A1* | 5/2003 | Tokito et al. ................ 428/690 |

FOREIGN PATENT DOCUMENTS

| EP | 0 443 861 B1 | 7/1995 |
| EP | 1 138 746 A1 | 10/2001 |
| WO | WO 00/70655 A2 | 11/2000 |
| WO | WO 01/41512 A1 | 6/2001 |
| WO | WO 01/96454 A1 | 12/2001 |
| WO | WO 02/02714 A2 | 1/2002 |

(Continued)

OTHER PUBLICATIONS

Journal of Polymer Science, Polymer Letters Edition, (1976), 14(11), pp. 653-659.*
O'Brien, D.F. et al., Electrophosphoresence from a doped polymer light emitting diode, Synthetic Metals, 116, (1-3), (2001) 379-383.

(Continued)

*Primary Examiner*—Dawn L. Garrett
(74) *Attorney, Agent, or Firm*—John H Lamming

(57) ABSTRACT

The present invention relates to polymeric metal complexes comprising metallic complexes covalently bound to conjugated polymers and luminescent materials containing such polymeric metal complexes. The invention further relates to electronic devices in which the active layer includes such polymeric metal complexes.

38 Claims, 10 Drawing Sheets

FOREIGN PATENT DOCUMENTS

| WO | WO 02/31896 A2 | * | 4/2002 |
| WO | WO 03/080687 A1 | | 10/2003 |
| WO | WO 03/091355 A2 | * | 11/2003 |

OTHER PUBLICATIONS

Campbell, I.H. et al., Excitation transfer processes in a phosphor-doped poly(p-phenylene vinylene) light-emitting diode, Physcial Review B, vol. 65, 08510, 2002, 085210-1—085210-8.

* cited by examiner (IX)

(X)

(XI)

(XII)

(XX)

(XXI)

(XXII)

(XXIII)

(XXIV)

(XXV)

(XXVI)

XXVII)

(XXVIII)

(XXIX)

(XXX)

(XXXI)

(XXXII)

METALLIC COMPLEXES COVALENTLY BOUND TO CONJUGATED POLYMERS AND ELECTRONIC DEVICES CONTAINING SUCH COMPOSITIONS

RELATED U.S. APPLICATION

This application claims priority to provisional application, Ser. No. 60/399,934, dated Jul. 30, 2002.

BACKGROUND OF THE INVENTION

1. Field of the Invention

The present invention relates to polymeric metal complex compositions comprising metallic complexes covalently bound to conjugated polymers. The invention further relates to electronic devices in which the active layer includes such polymeric metal complex compositions.

2. Description of the Related Art

Organic electronic devices that emit light, such as light-emitting diodes that make up displays, can be used in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of a voltage across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as had been disclosed in, for example, Friend et al., U.S. Pat. No. 5,247,190, Heeger et al., U.S. Pat. No. 5,408,109, and Nakano et al., Published European Patent Application 443 861. Polymeric materials with stilbenyl or oxadiazole side chains have been reported by Holmes et al., U.S. Pat. No. 5,653,914. Complexes of 8-hydroxyquinolate with trivalent metal ions, particularly aluminum, have been extensively used as electroluminescent components, as has been disclosed in, for example, Tang et al., U.S. Pat. No. 5,552,678. Complexes of Iridium with phenylpyridine, phenylquinoline, or phenylpyrimidine ligands have been disclosed as electroluminescent compounds in Petrov et al., Published PCT Application 02/02714.

Electroluminescent devices with an active layer of polyvinyl carbazole (PVK) doped with metallic complexes of iridium have been described by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. No. 6,303,238, Bradley et al., in Synth. Met. (2001), 116 (1–3), 379–383, and Campbell et al., in Phys. Rev. B, Vol. 65 085210.

Small molecule light-emitting materials are usually deposited by evaporative techniques. The equipment required for such processes can be quite expensive and may not be adaptable to continuous processing. Small molecule light-emitting materials can be coated from solution. However, they have a tendency to crystallize with evaporation of the coating solvent, which reduces their electroluminescent effectiveness.

There is a continuing need for electroluminescent materials having improved electrical efficiency.

SUMMARY OF THE INVENTION

The present invention is directed to a polymeric metal complex composition comprising (a) a conjugated polymeric backbone; (b) a plurality of first-type functional groups; and (c) a plurality of first-type inert spacer groups, wherein each, of the plurality of first-type functional groups is covalently bound to at least one of the plurality of first-type inert spacer, groups, which first-type inert spacer group is covalently bound to the polymeric backbone, and wherein at least a portion of each of the plurality of first-type functional groups is coordinated to at least one metal.

In one embodiment, the present invention is directed to an electroluminescent material containing at least one polymeric metal complex.

In another embodiment, the present invention is directed to an organic electronic device comprising at least one polymeric metal complex of the present invention.

As used herein, the term "conjugated" is intended to mean an unsaturated organic system having adjacent atoms with pi electrons where there is extended pi overlap across the system. The atoms can be $sp^2$ or $sp$ hydbridized carbon atoms or other atoms with unshared electron pairs which can be hybridized into p orbitals. The term "inert spacer group" is intended to mean a connecting organic group that does not provide direct conjugation from one end point to the other end point. The term "compound" is intended to mean an electrically uncharged substance made up of molecules that further consist of atoms, wherein the atoms cannot be separated by physical means. The term "ligand" is intended to mean a molecule, ion, or atom that is attached to the coordination sphere of a metallic ion. The term "parent ligand compound" is intended to mean the neutral compound from which an ionic ligand is derived. The term "complex", when used as a noun, is intended to mean a compound having at least one metallic ion and at least one ligand. The term "functional group" is intended to mean a group that is capable of coordinating to a metal ion or atom. The term "functionalized polymer" is intended to mean a polymer having at least one functional group(s) prior to complexation with a metal. The term "precursor metal compound" is intended to mean a metal compound before it is attached to the functionalized polymer. The term "polymeric metal complex" is intended to mean polymeric material containing first-type functional groups where at least a portion of the first-type functional groups are coordinated to at least one metal containing complex. The term "β-dicarbonyl" is intended to mean a neutral compound in which two ketone groups are present, separated by a CHR group. The term "β-enolate" is intended to mean the anionic form of the β-dicarbonyl in which the proton from the CHR group between the two carbonyl groups has been abstracted. The term "group" is intended to mean a part of a compound, such as a substituent in an organic compound or a ligand in a complex. The term "coordinated" is intended to mean that one atom of a functional group forms a bond with a metal atom, where the functional group atom is a Lewis base donor atom, and the metal atom is a Lewis acid acceptor atom. The prefix "hetero" indicates that one or more carbon atoms has been replaced with a different atom. The term "arylene" is intended to mean a group derived from an aromatic hydrocarbon having two points of attachment, which group may be unsubstituted or substituted. The term "heteroarylene" is intended to mean a group derived from an aromatic group having at least one heteroatom and having two points of attachment, which group may be unsubstituted or substituted. Unless otherwise indicated, all groups can be unsubstituted or substituted. The term "luminescence" is intended to mean the emission of light without high temperature or incandescence. The adjective "luminescent" refers to materials which exhibit luminescence. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). The term "(H+F)" is intended to mean all combinations of hydrogen and fluorine, including completely hydrogenated, partially fluorinated or perfluorinated substituents. By "emission maximum" is meant the wavelength, in nanometers, at which the maximum intensity of electroluminescence is obtained. Electroluminescence is generally measured in a diode structure, in which the material to be tested is sandwiched between two electrical contact layers and a voltage is applied. The light intensity and wavelength can be measured, for example, by a photodiode and a spectrograph, respectively. In addition, the IUPAC numbering system is used throughout, where the groups from the Periodic Table are numbered from left to right as 1 through 18 (CRC Handbook of Chemistry and Physics, 81$^{st}$ Edition, 2000).

DETAILED DESCRIPTION OF THE PREFERRED EMBODIMENTS

The polymeric metal complex has a composition in which there is a covalent attachment between the metal complex and the conjugated polymer. The polymeric metal complex is formed by coordinating a precursor metal complex to a functionalized polymer, where the functionalized polymer comprises a conjugated polymeric backbone, a plurality of first-type functional groups, and inert spacer groups linking the first-type functional groups to the conjugated polymeric backbone.

The conjugated polymeric backbone facilitates charge transport. A suitable polymeric backbone should have sufficient conjugation to achieve good transport properties. The polymeric backbone, in the absence of the metallic complex, can be luminescent itself, or it can be non-luminescent.

Figure 1:
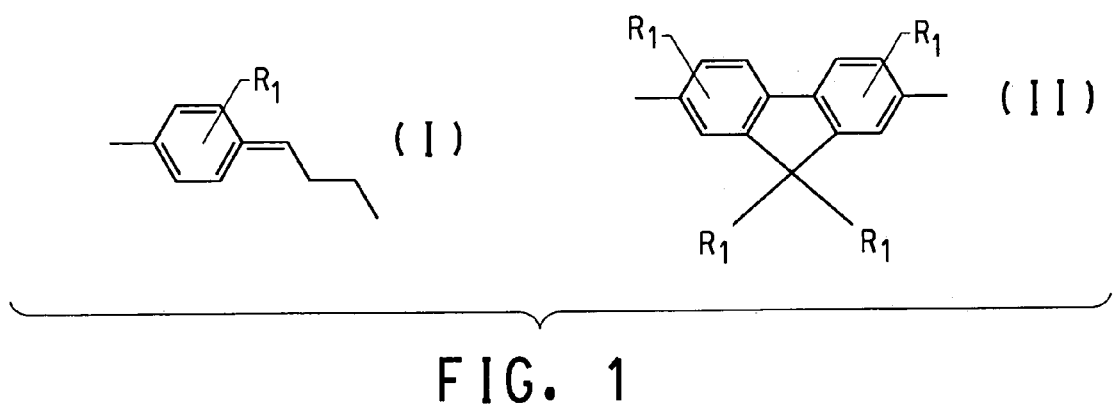
FIG. 1 shows Formulae I and II for repeating units of conjugated polymeric backbones of the invention.

Conjugated polymers are well known and have been studied extensively. The polymeric backbone can be a homopolymer or a copolymer, and can be substituted or unsubstituted. Examples of suitable conjugated polymeric backbones include polyphenylenes, polypyridines, polyarylamines, polyphenylenevinylenes, polyfluorenes, polyoxadiazoles, polythiophenes, and copolymers thereof. If the polymeric backbone has a non-conjugated portion, that portion may also provide charge transport properties, such as with vinylcarbazolediyl or triarylmethanediyl monomeric units. Other non-conjugated segments can be, for example, acrylic, methacrylic, vinyl, or other known monomeric units. The conjugated polymer is preferably a polyphenylene vinylene having at least one repeating unit having Formula I, shown in FIG. 1, or a polyfluorene having at least one repeating unit having Formula II, shown in FIG. 1, where:

$R^1$ is a substituent on a carbon atom which can be the same or different at each occurrence and is selected from hydrogen, alkyl, aryl, heteroalkyl, heteroaryl, F, —CN, —$OR^2$, —$CO_2R^2$, $C_n(H+F)_{2n+1}$, —$OC_n(H+F)_{2n+1}$, —$SR^2$, —$N(R^2)_2$, —$P(R^2)_2$, —$SOR^2$, —$SO_2R^2$, —$NO_2$; or adjacent $R^1$ groups together can form a 5- or 6-membered cycloalkyl, aryl, or heteroaryl ring, and $R^2$ is a substituent on a heteroatom which can be the same or different at each occurrence and is selected from alkyl, aryl, heteroalkyl and heteroaryl; and n is an integer from 1 through 12.

The preferred $R^1$ groups are alkyl groups having from 1 to 12 carbon atoms, heteroalkyl groups having 1 to 12 carbon atoms and one or more heteroatoms of S, N, or O, aryl groups having from 6 to 20 carbon atoms, and heteroaryl groups having from 2 to 20 carbon atoms and one or more heteroatoms of S, N, or O. Examples of suitable $R^1$ groups include n- and iso-butyl, pentyls, both linear and branched, hexyls, octyls, including 2-ethylhexyl, up through hexadecyls and above, with and without olefinic unsaturation; phenyl, thiophene, carbazole, alkoxy, phenoxy and cyano groups. More preferred $R^1$ groups on the phenyl ring of the phenylenevinylene polymer are H, $C_1$ through $C_{12}$ alkoxy, $C_1$ through $C_{12}$ alkyl, $C_6$ through $C_{12}$ aryl and $C_6$ through $C_{25}$ alkoxy-substituted aryls. More preferred $R^1$ groups on the carbon atom in the 9-position of the fluorene repeating unit are linear and branched $C_6$ through $C_{12}$ alkyls. More preferred $R^1$ groups on the phenyl rings of the fluorene repeating unit are H, $C_6$ through $C_{12}$ alkoxy, phenoxy, $C_6$ through $C_{12}$ alkyl, phenyl or cyano.

Figure 2:
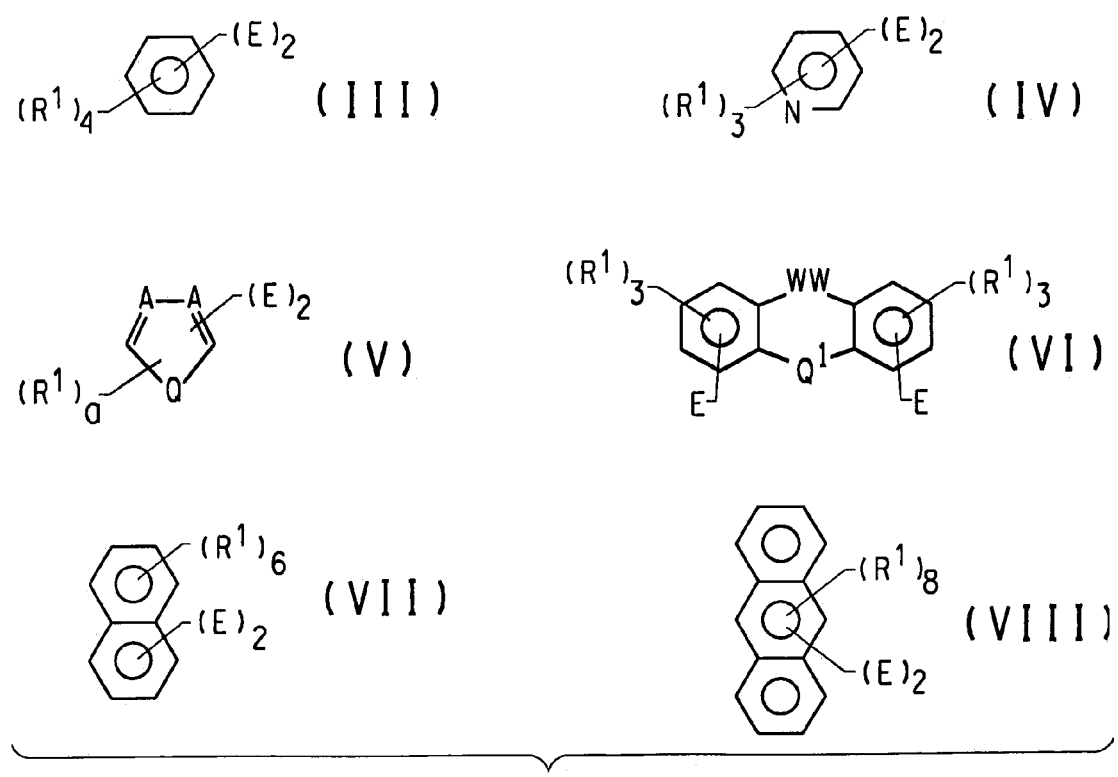
FIG. 2 shows Formulae III through VII for repeating units of conjugated polymeric backbones of the invention.
Figure 3:
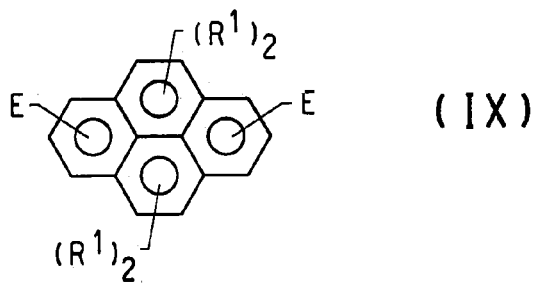
FIG. 3 shows Formulae IX through XII for repeating units of conjugated polymeric backbones of the invention.
Figure 3:
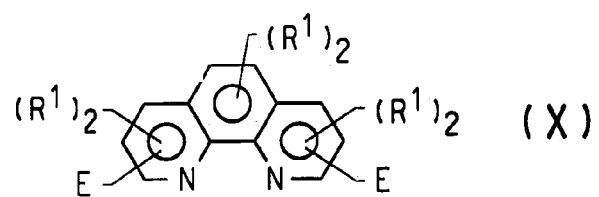
Figure 3:
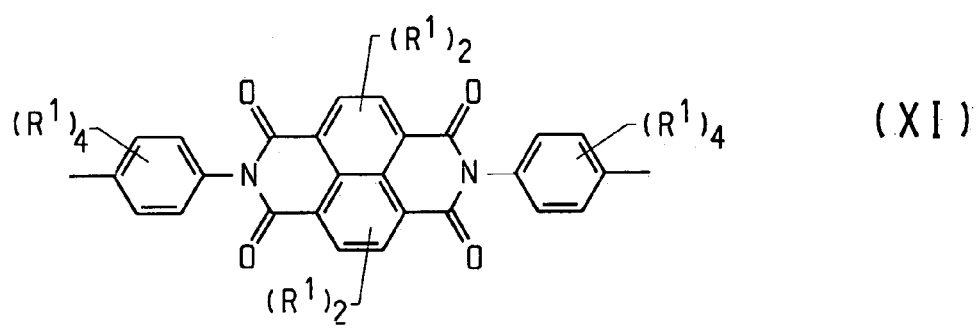
Figure 3:
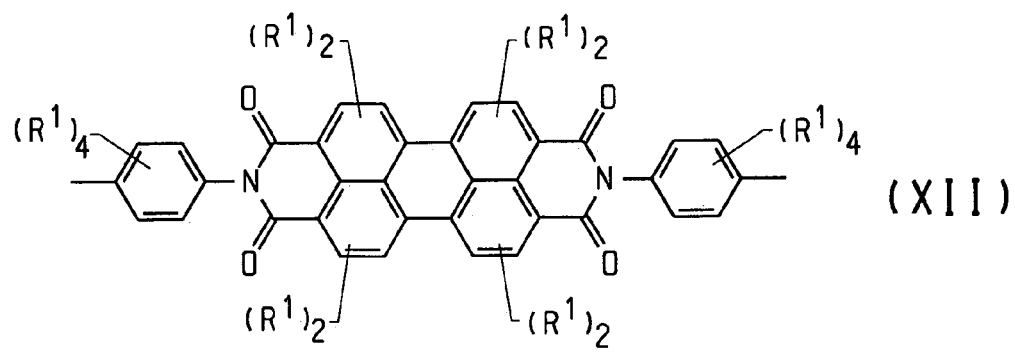

Suitable fluorene copolymers can include additional repeating units selected from Formulae III through XII, shown in FIGS. 2 and 3, where $R^1$ and $R^2$ are as defined above, and in each of Formulae II, IV, V, VI, VII, VIII, IX, and X:

E can be the same or different at each occurrence and is a single bond or a linking group selected from arylene and heteroarylene;

in Formula V:
A is independently at each occurrence C or N and γ is 0 or an integer selected from 1 or 2, such that when both A are N, then γ is 0; or when one of A is N and one of A is C, then γ is 1; or when both A are C, then γ is 2; Q is O, S, $SO_2$, or $NR^2$;
in Formula VI:
$Q^1$ is a carbonyl group, O, S, $SO_2$, or $NR^2$;
W is H, alkyl or heteroalkyl; or both of W together can represent one single bond;
in Formula VII:
the two E's are in the 1,4-, 1,5-, 1,8-, 2,3-, or 2,6- positions;
in Formula VIII:
the two E's are in the 1,4-, 1,5-, 1,8-, 2,3-, 2,6-, or 9,10-positions;
in Formula IX:
a first E is in the 1, 2, or 3 position, a second E is in the 6, 7, or 8 position;
in Formula X:
a first E is in the 2, 3, or 4 position; a second E is in the 7, 8, or 9 position.

The first-type functional group is a group that is capable of coordinating to a metal. Useful first-type functional groups generally contain at least one nitrogen, oxygen, phosphorus or sulfur atom. Examples of suitable first-type functional groups include: carboxylic acid groups, or the acid salt; sulfuric acid groups, or the acid salt; groups having an —OH moiety, such as alkoxyl and phenoxyl; primary, secondary and tertiary amines; imines and diimines, such as pyridine, bipyridine and phenanthroline, and derivatives, including their oxides; phosphines; phosphine oxides; β-dicarbonyl groups, nitriles and isonitriles, cyanates, isocyanates, and any other coordinating groups. Preferred first-type functional groups are carboxylic acid, sulfonic acid, alkoxyl, bipyridine, phenanthroline, and β-dicarbonyl. It should be understood that the composition of a first-type functional group in the functionalized polymer may be identical to or different from the composition of another first-type functional group in the same functionalized polymer.

The first-type functional group is attached to the conjugated backbone with at least one first-type inert spacer group.

In the polymeric metallic complex, at least one metal ion or atom is coordinated to a plurality of ligands, at least one of which is the first-type functional group on the conjugated polymeric backbone. The nature of the other ligands can, in some cases, affect the luminescence strength, wavelength, efficiency and other properties of the electroluminescent material. The other ligands are discussed in more detail below.

Preferred metals are the lanthanide metals, the Group 7, 8, 9, 10, and 11 transition metals, and the Group 12 and 13 metals Particularly preferred metals are europium, terbium, thulium, rhenium, ruthenium, osmium, rhodium, iridium, platinum, palladium, gold, aluminum and zinc. Most preferred, are iridium and platinum.

Polymeric-metal complexes of the present invention can be obtained from combining at least one functionalized polymer with at least one precursor metal compound.

I. Functionalized Polymer

The functionalized polymeric compounds that are useful in the present invention can be generally described as having: (a) a conjugated polymeric backbone; (b) a plurality of first-type functional groups; (c) a plurality of first-type inert spacer groups, wherein each of the pluarity of first-type functional groups is attached to at least one of the plurality of the first-type spacer group, which first-type inert spacer groups are attached to the polymeric backbone; and optionally (d) a plurality of second-type functional groups.

The number of first-type functional groups in the functionalized polymer, which also can be described as the "density of functional groups", will determine the "maximum loading of the metal complex" (the amount of metal that can be coordinated to the functionalized polymer).

The functionalized polymer can also have second-type functional groups. The second-type functional groups can be present to modify the physical processing properties or the photophysical properties of the final polymeric metal complex. Examples of groups which modify the processing properties include plasticizing groups, such as alkylene oxide groups, and reactive and/or crosslinkable groups, such as terminal vinyl groups and epoxy groups. Examples of groups which modify the photophysical properties include charge transport groups, such as carbazole or oxadiazole groups. The second-type functional groups can be covalently attached directly to the polymer backbone, or it can be attached to second-type inert spacer groups, which is covalently attached to the polymer backbone.

Both the first-type inert spacer groups and the second-type inert spacer groups are spacer groups that are not conjugated with the conjugated polymeric backbone. Preferably, the inert spacer groups do not contain any atoms with pi electrons. Examples of useful inert spacer groups include alkyl chains of from 1 through 12 carbon atoms, preferably 4 through 12. The inert spacer groups can also contain ether, ester, thioether, amide, imine, amine, or aromatic constituents, provided that such groups do not extend the conjugation of the polymeric backbone to the emissive center of the metal complex.

The functionalized polymer may contain inert spacer groups that are the same or different in composition from each other. For example, the functionalized polymer may have first-type spacer groups that have compositions different from each other. Where second-type of inert spacer groups are also present, the second-type inert spacer groups may be the same or different in composition from each other, and from the first-type inert spacer groups. Each inert spacer group is attached to one or more first-type functional groups. Similarly, each second-type inert spacer group is attached to one or more second-type functional groups. If the spacer group is branched, it could be covalently bound to more than one functional groups. It is possible that the same spacer group may be covalently bound to both a first-type functional group and a second-type functional group. In another embodiment, each of the first-type functionalized group is covalently bound to one first-type inert spacer group, such that the ratio of the number of first-type functionalized group to the number of first-type spacer group is 1:1.

Similarly, in another embodiment, each of the second-type functionalized group is covalently bound to one second-type inert spacer group such that the ratio number of the second-type functionalized group to the number of second-type inert spacer group is 1:1.

It is further understood that the term "plurality of" component is intended to encompass components of the same or different composition. Therefore, for example, in one embodiment the functionalized polymer may have first-type functional groups having the same composition from each other, while in another embodiment the functionalized polymers may have first-type functional groups having various compositions, which results in polymer metal complexes having first-type functional group having various compositions. The present invention further encompasses second-type functional groups having identical and various compositions.

The functionalized polymer can be made by polymerizing monomer(s) having the desired functional group(s) attached with a spacer group, using conventional polymerization techniques. Alternatively, a polymer can be formed having spacer groups that are covalently attached to a first reactive group. The functional groups can be added to polymeric backbones by reacting a compound having the functional group and a second reactive group with the polymer having the first reactive group. For example, a compound having the functional group and an acid chloride group can be reacted with a polymer with spacer groups attached to hydroxyl functional groups, to form an ester linkage between the spacer group and the functional group. Alternatively, the acid chloride group can be the functional group attached to a spacer group on a polymer and can be reacted with a compound having an hydroxyl group. A variety of synthetic routes are available in the organic chemistry literature.

For the polymeric metal complex materials of the invention, the density of first-type functional groups is determined by the relative proportion of monomers having first-type functional groups ("first-type functional monomers") to monomers not having functional groups ("nonfunctional monomers") in the polymer. In general, the ratio of first-type functional monomers to non-functional monomers can be in the range of about 100:0 (no non-functional monomers) to 0.1:99.9. In general, the amount of metal in the polymeric metal complex is about 0.1 to 10% by weight, based on the total weight of the polymeric metal complex.

II. Precursor Metal Compound

The precursor metal compound is one which will coordinate to the first-type functional group on the functionalized polymer and provide the desired property(ies), luminescence and/or charge transport, in the final polymeric-metal complex. The precursor metal compound can be a simple metal salt, optionally in the presence of additional ligands, or it can be a metal complex. In some cases the precursor metal complexes may be present in more than one isomeric form, or mixtures of different complexes may be present. It will be understood that the term "precursor metal compound" is intended to encompass mixtures of compounds and/or isomers. It is also possible to use two or more different metals to coordinate to the functionalized polymer.

Appropriate metal complexes include and metal/ligand combinations which produce a high photoluminescent quantum yield, preferably greater than 10%. Some typical examples include Al or Zn complexes of quinolinato or polydentate Schiff base ligands. More preferred, are metal/ligand combinations which also give rise to short-lived, i.e., less than 10 microseconds, triplet excited states. Some examples are noble metal complexes, such as Ir, Pt, Ru, Re, Os, or Au, with cyclometallated ligands, such as phenylpyridines, imine ligands, such as bipyridine, or phosphine ligands such as triphenylphosphine; and rare earth metals such as Eu and Tb, in combination with acetylacetonate-derived ligands.

The polymeric-metal complexes of the invention will be described in terms of four representative types of metals: lanthanides, iridium, platinum, and aluminum.

1. Lanthanide Metals

Figure 4:
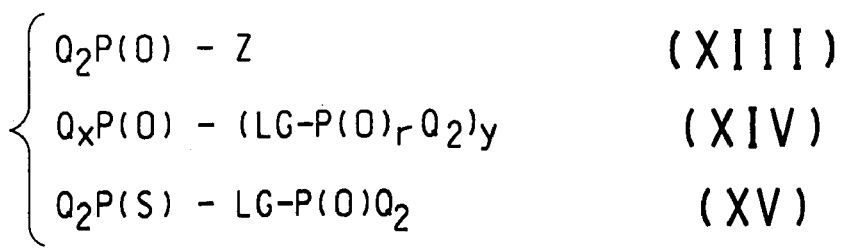
FIG. 4 shows Formulae XII through XV for ligands useful in the invention.
Figure 5:
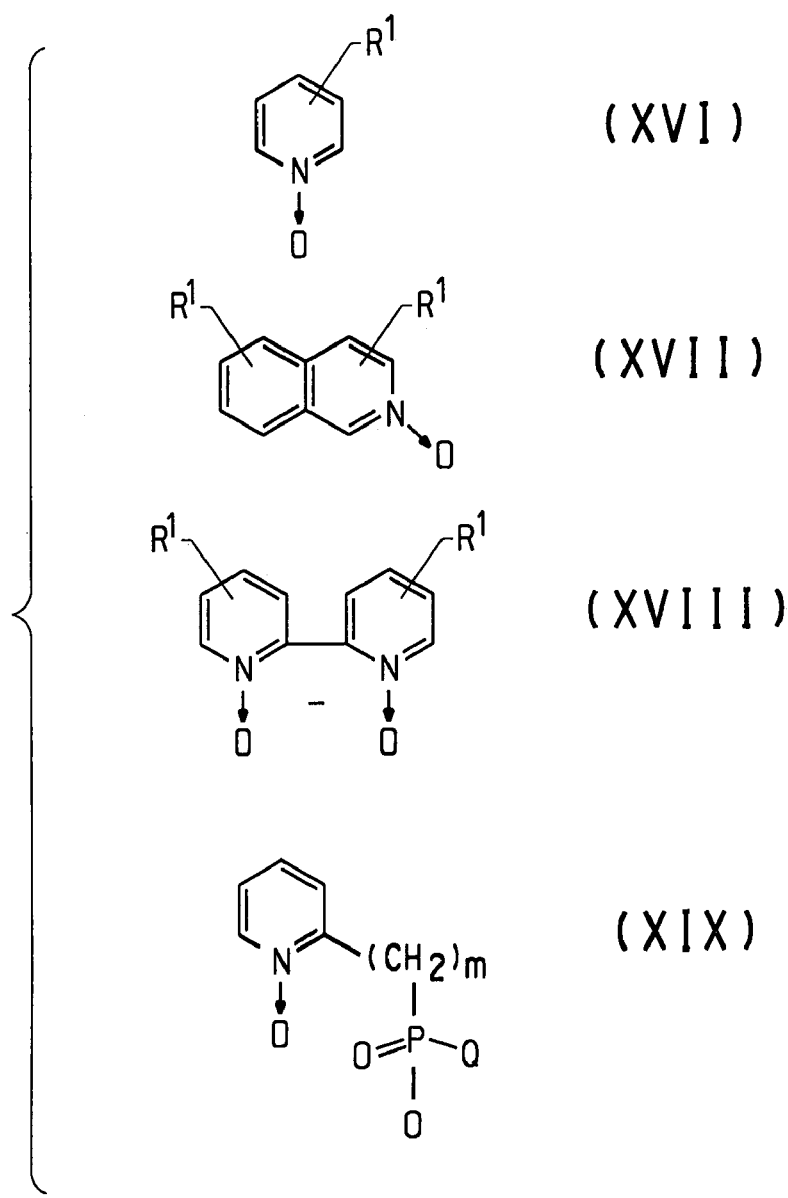
FIG. 5 shows Formulae XVI through XIX for ligands useful in the invention.
Figure 6:
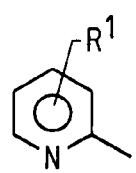
FIG. 6 shows Formulae XX and XXI for ligands useful in the invention.
Figure 6:
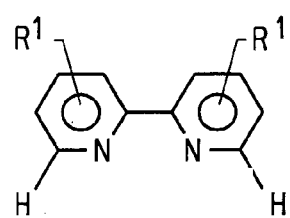

It is preferred that, in the polymeric-metal complex, the lanthanide metal is coordinated to at least one ligand selected from monophosphine oxides having Formula XII shown in FIG. 4; bisphosphine dioxides having Formula XIV, shown in FIG. 4, where in Formula XIV, x is 2, y is 1, and r is 1, or where x is 1, y is 2, and r is 0; trisphosphine trioxide having Formula XIV, shown in FIG. 4, where in Formula XIV, x is 1, y is 2, and r is 0; bis-phosphine oxide-sulfides having Formula XV, shown in FIG. 4; pyridine N-oxides having Formula XVI, Formula XVII or Formula XVIII, shown in FIG. 5; phosphine oxide-pyridine N-oxides having Formula XIX, shown in FIG. 5; a mono-imine having a Formula XX, shown in FIG. 6, and a diimine having a Formula XXI, shown in FIG. 6, where:

in each of Formulae XIII, XIV and XV:

$Q^2$ is the same or different at each occurrence and is selected from $C_6H_sF_{5-s}$, and $C_n(H+F)_{2n+1}$, n is an integer from 1 through 12, and s is 0 or an integer from 1 through 5, in Formula XIII:

Z is selected from $Q^2$ and pyridyl, in each of Formulae XIV and XV:

LG is the same or different at each occurrence and is a linking group selected from $C_n(H+F)_{2n}$, arylene, cyclic heteroalkylene, heteroarylene, alkyleneheteroarylene, ferrocenediyl, and o-carboranediyl, in Formula XIV:

r is the same or different at each occurrence and is 0 or 1, x is 1 or 2, and y is 1 or 2, with the provision that x+y=3, in each of Formulae XVI through XXI:

$R^1$ is as defined above, in Formula XIX:

m is 0 or an integer from 1 through 12.

As used herein, the term "phosphine oxide ligand" is intended to mean a ligand having one or more phosphine oxide groups, hereinafter shown as "P(O)". The term "bis-phosphine oxide-sulfide ligand" is intended to mean a ligand having one phosphine oxide group and one phosphine sulfide group, where the phosphine sulfide group is hereinafter shown as "P(S)". The term "pyridine N-oxide ligand" is intended to mean a ligand having a substituted or unsubstituted pyridine N-oxide fragment. The term "phosphine oxide-pyridine N-oxide" is intended to mean a ligand having one phosphine oxide group and one pyridine N-oxide fragment.

Examples of suitable monophosphineoxide ligands include:

tris(pentafluorophenyl)phosphine oxide [tpfpO]; (diphenyphosphinomethyl)diphenylphosphine oxide [dppmO]; (diphenyphosphinoethyl)diphenylphosphine oxides

[dppeO]; (diphenyphosphinopropyl)diphenylphosphine oxides [dpppO]; (diphenyphosphinobutyl)diphenylphosphine oxides [dppbO]; bis(diphenylphosphinomethyl) phenylphosphineoxide [bisdppmO]; and bis(diphenylphosphinoethyl)phenylphosphine oxide [bisdppeO].

Examples of suitable diphosphine dioxide ligands include:

bis(diphenylphosphino)methane dioxide [dppmO2];

1,2-bis(diphenylphosphino)ethane dioxide [dppeO2];

1,3-bis(diphenylphosphino)propane dioxide [dpppO2];

1,4-bis(diphenylphosphino)butane dioxide [dppbO2];

1,1'-bis(diphenylphosphino)ferrocene dioxide [dppFeO2];

1,2-bis(di(pentafluorophenyl)phosphino)ethane dioxide [F5dppeO2]; and bis(diphenylphosphinoethyl)phenyl phosphine dioxides [bisdppeO2].

where the plural term "oxides" is used to indicate that multiple isomers are possible and may be present.

The oxides of monodentate phosphines, dioxides of bidentate phosphines (except for dppfcO$_2$ and dppcbO$_2$), and trioxides of tridentate phosphines are generally prepared by the oxidation of the corresponding phosphine with aqueous hydrogen peroxide in ethanol, as described in: Ellermann, J.; Schirmacher, D. *Chem. Ber.* 1967, 100, 2220; Siegl, W. O.; Lapporte, S. J.; Collman, J. P. *Inorg. Chem.* 1971, 10, 2158; Lindner, E.; Beer, H. *Chem. Ber.* 1972, 105, 3261. The hydrogen peroxide oxidation is also used to prepare dppcbO$_2$, but in THF at room temperature.

The bis-phosphine monoxides can be synthesized via the selective Pd-catalyzed biphasic anaerobic oxidation of the corresponding bidentate phosphines with 1,2-dibromoethane in the presence of alkali, as described in: Grushin, V. V. *J. Am. Chem. Soc.* 1999, 121, 5831; U.S. Pat. No. 5,919,984, 1999. This Pd-catalyzed oxidation is also applied to the preparation of dppfcO$_2$.

The phosphine oxide group can be attached to a polymeric backbone by a variety of synthetic routes available in the organic chemistry literature.

Examples of suitable N-oxide ligands include, but are not limited to:
  pyridine N-oxide [pyo];
  3-cyanopyridine N-oxide [CNpyO]; and
  bipyridine bis(N-oxide) [bipyO2].

Some N-oxide compounds are commercially available. Others can be made by oxidizing a nitrogen containing ligand with oxidants such as, for example, hydrogen peroxide.

The N-oxides can be attached to a polymeric backbone using known synthetic techniques. In some cases it is possible to attach the nitrogen-containing ligand and then oxidize.

Examples of suitable mono-imines include:
  3-cyanopyridine [3-CNpy];
  2-dimethylaminopyridine [2-dmapy];
  isoquinoline [isoq];
  4-tertbutyl-pyridine [4-tbpy];
  4-phenylpyridine [4-phpy]; and
  2-(2-thienyl)pyridine [2-tpy].

Examples of suitable diimines include:
  5,5'-bis(trifluoromethyl)-2,2'-bipyridine [FMbipy];
  4,4'-bis(2-trifluoromethylphenyl)-2,2'-bipyridine [2-FMPbipy];
  4,4'-bis(3-trifluoromethylphenyl)-2,2'-bipyridine [3-FMPbipy]; and
  bis(4-fluorophenyl)-2,2'-bipyridine [FPbipy].

In some cases, the diimine and mono-imine ligands are commercially available from, for example, Aldrich Chemical Company (Milwaukee, Wis.). "FMbipy" can be prepared according to: Furue, Masaoki; Maruyama, Kazunori; Oguni, Tadayoshi; Naiki, Masahiro; Kamachi, Mikiharu. *Inorg. Chem.* 1992, 31(18), 3792–5. "2-FMPbipy", "3-FMPbipy", and "FPbipy" can be prepared by Suzuki coupling, according to analogous literature procedures found in: Damrauer, Niels H.; Boussie, Thomas R.; Devenney, Martin; McCusker, James K. *J. Am. Chem. Soc.* 1997, 119(35), 8253–8268.

The above-described ligands can be added separately, or they can be present as the first-type functional group on the polymer. The remaining coordination sites are preferably occupied by β-enolate ligands. As with the other ligands, the β-enolate ligands can be present separately, or as the first-type functional group on the polymer.

Figure 7:
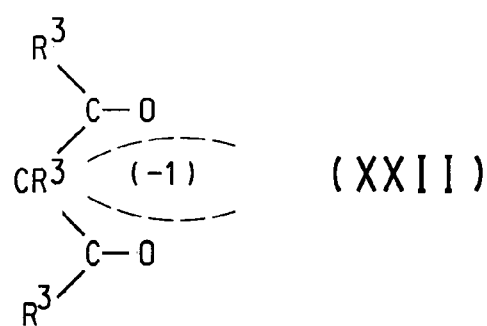
FIG. 7 shows Formula XXII for a ligand useful in the invention.

The β-enolate ligands generally have Formula XXII shown in FIG. 7, where R$^3$ is the same or different at each occurrence. The R$^3$ groups can be hydrogen, halogen, substituted or unsubstituted alkyl, aryl, alkylaryl or heterocyclic groups, or OR$^2$ groups, where R$^2$ is as defined above. Adjacent R$^3$ groups can be joined to form five- and six-membered rings, which can be substituted. Preferred R$^3$ groups are selected from H, F, C$_n$(H+F)$_{2n+1}$, —OC$_n$(H+F)$_{2n+1}$, —OC$_n$(H+F)$_{2n}$—, —C$_6$H$_5$, —C$_4$H$_3$S, and —C$_4$H$_3$O, where n is an integer from 1 to 12, preferably from 1 to 6.

The β-enolate ligands are derived from β-dicarbonyl parent ligand compounds. Examples of suitable β-dicarbonyl parent ligand compounds, include the compounds listed below. The abbreviation for the β-enolate form is given below in brackets:
  2,4-pentanedionate [acac];
  1,3-diphenyl-1,3-propanedionate [DI];
  2,2,6,6-tetramethyl-3,5-heptanedionate [TMH];
  4,4,4-trifluoro-1-(2-thienyl)-1,3-butanedionate [TTFA];
  7,7-dimethyl-1,1,1,2,2,3,3-heptafluoro-4,6-octanedionate [FOD];
  1,1,1,3,5,5,5-heptafluoro-2,4-pentanedionate [F7acac];
  1,1,1,5,5,5-hexaflouro-2,4-pentanedionate [F6acac]; and
  1-phenyl-3-methyl-4-i-butyryl-pyrazolinonate [FMBP].

The β-dicarbonyl parent compounds are generally available commercially. The parent compound of F7acac, 1,1,1,3,5,5,5-heptafluoro-2,4-pentanedione, CF$_3$C(O)CFHC(O)CF$_3$, can be prepared using a two-step synthesis, based on the reaction of perfluoropentene-2 with ammonia, followed by a hydrolysis step. This compound should be stored and reacted under anyhydrous conditions as it is susceptible to hydrolysis.

2. Iridium

Figure 8:
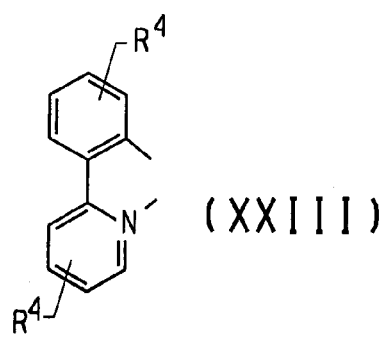
FIG. 8 shows Formulae XXIII through XXVII for ligands useful in the invention.
Figure 8:
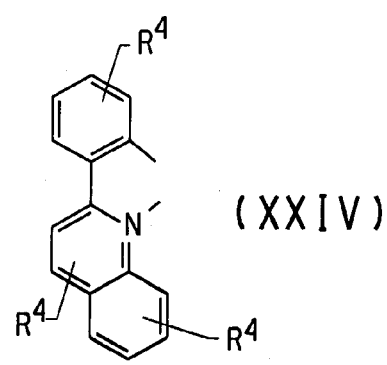
Figure 8:
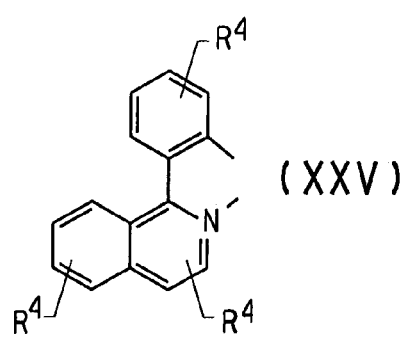
Figure 8:
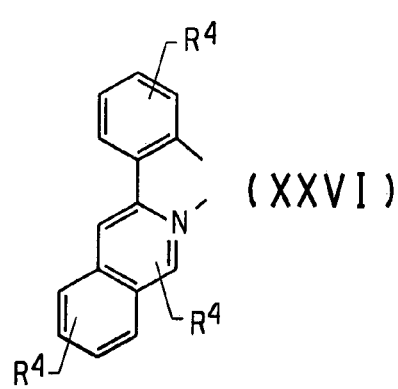
Figure 8:
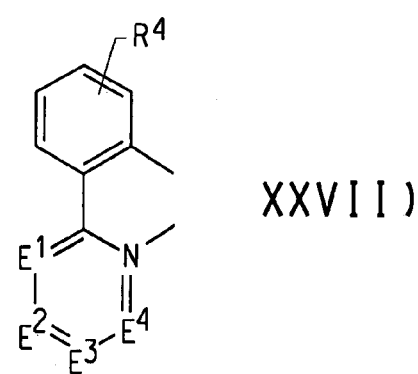
Figure 9:
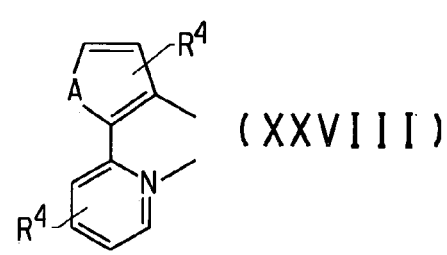
FIG. 9 shows Formulae XXVIII through XXXII for ligands useful in the invention.
Figure 9:
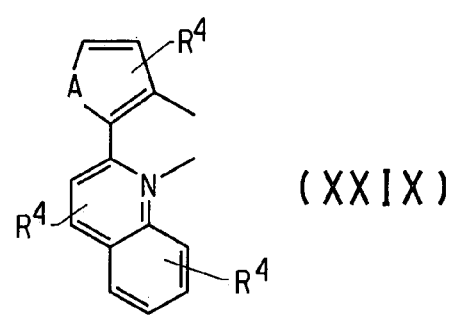
Figure 9:
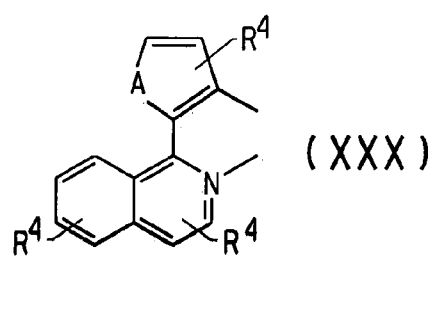
Figure 9:
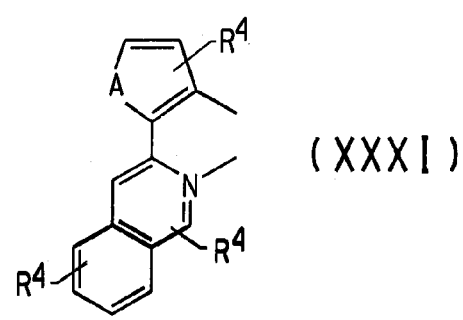
Figure 9:
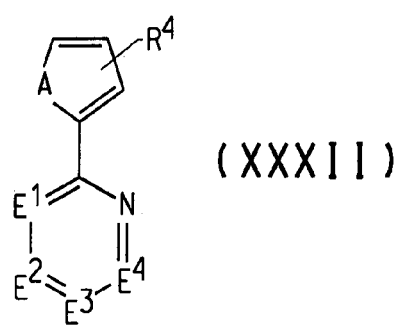

The polymeric-metal complexes with iridium metal are preferably made from precursor iridium compounds which are complexes having at least one ligand, L, which is selected from Formulae XXIII through XXVII, shown in FIG. 8, and from Formulae XXVIII through XXXXII, shown in FIG. 9, where:
  at each occurrence in any of Formulae XXIII through XXXII:
    R$^4$ is the same or different at each occurrence and is selected from H, D, C$_n$H$_{2n+1}$, OR$^5$, SR$^5$, N(R$^5$)$_2$, F, C$_n$(H+F)$_{2n+1}$, OC$_n$(H+F)$_{2n+1}$, and OCF$_2$Y, or adjacent pairs of R$^4$ can be joined to form a five- or six-membered ring;
    R$^5$ is the same or different at each occurrence and is H or C$_n$H$_{2n+1}$;
    n is an integer from 1 through 12; and
    Y is Cl, or Br; and
  at each occurrence in any of Formulae XXVIII through XXXII:
    A is S or NR$^5$;
  at each occurrence in any of Formula XXVII and Formula XXXII:
    E$^1$ through E$^4$ are the same or different and are N or CR$^6$, with the proviso that at least one E is N; and
    R$^6$ is the same or different at each occurrence and is selected from H, D, SR$^5$, N(R$^5$)$_2$, F, C$_n$(H+F)$_{2n+1}$, OC$_n$(H+F)$_{2n+1}$, and OCF$_2$Y, or adjacent pairs of R$^6$ can be joined to form a five- or six-membered ring.

Ligand L having Formula XXIII, shown in FIG. 8, is derived from a phenylpyridine compound. Ligand L having Formula XXIV, shown in FIG. 8, is derived from a phenylquinoline compound. Ligand L having Formula XXV or Formula XXVI, shown in FIG. 8, is derived from a phenyl-isoquinoline compound. Ligand L having formula XXVII, shown in FIG. 8, is derived from a phenyl-diazine compound, or the analog with 2 or more nitrogens. In Formulae XXIII through XXVII, it is preferred that there is at least one substituent on one of the rings selected from F, Cn $(H+F)_{2n+1}$, and $OC_n(H+F)_{2n+1}$.

Ligand L having Formula XXVIII, shown in FIG. 9, is derived from a thienyl-pyridine (when A is S) or pyrrolyl-pyridine (when A is $NR^5$) compound. Ligand L having Formula XXIX, shown in FIG. 9, is derived from a thienyl- or a pyrrolyl-quinoline compound. Ligand L having Formula XXX or Formula XXXI, shown in FIG. 9, is derived from a thienyl- or a pyrrolyl-isoquinoline compound. Ligand L having Formula XXXII, shown in FIG. 9, is derived from a thienyl- or a pyrrolyl-diazine compound, or the analog with 2 or more nitrogens. In Formulae XXVIII through XXXII, when A is $NR^5$, it is preferred that $R^5$ is $CH_3$. It is preferred that all the substituents on the thienyl or pyrrolyl ring are H or D. It is also preferred that there is at least one substituent on one of the nitrogen-containing rings selected from F, $Cn(H+F)_{2n+1}$, and $OC_n(H+F)_{2n+1}$.

Figure 10:
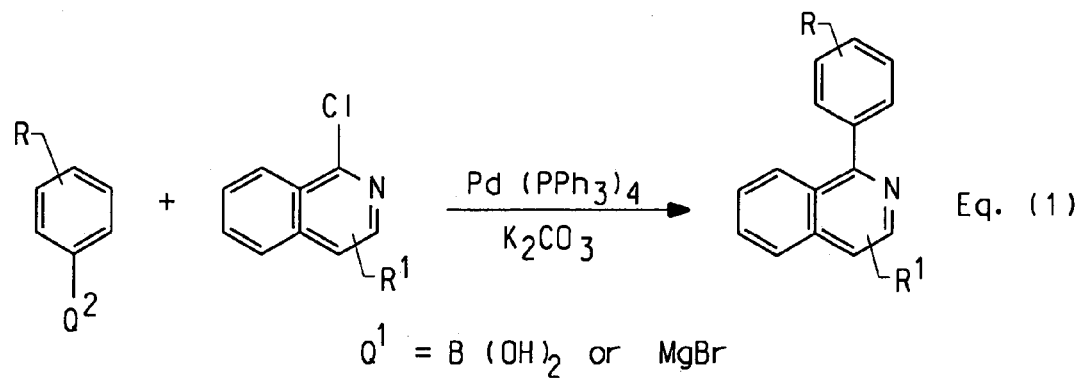
FIG. 10 shows Equation (1) for preparing a ligand.

The parent ligand compounds, HL, can generally be prepared by standard palladium-catalyzed Suzuki or Kumada cross-coupling of the corresponding heterocyclic aryl chloride with an organoboronic acid or organomagnesium-reagent, as described in, for example, O. Lohse, P. Thevenin, E. Waldvogel *Synlett*, 1999, 45–48. This reaction is illustrated for a phenyl-isoquinoline in Equation (1) in FIG. 10, where $R^1$ is as defined above.

Figure 11:
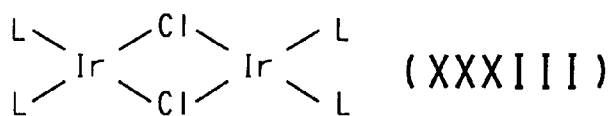
FIG. 11 shows Formulae XXXIII and XXXIV for iridium precursor complexes; and Equation (2) for preparing an iridium precursor complex.
Figure 11:
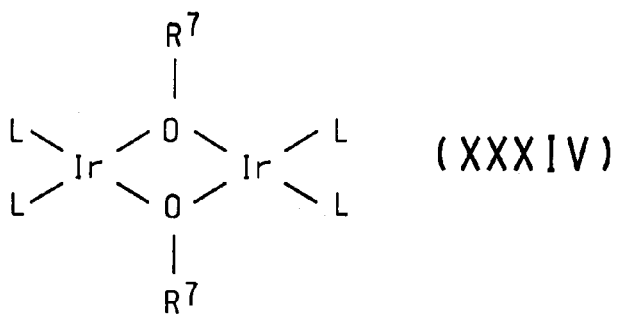
Figure 11:
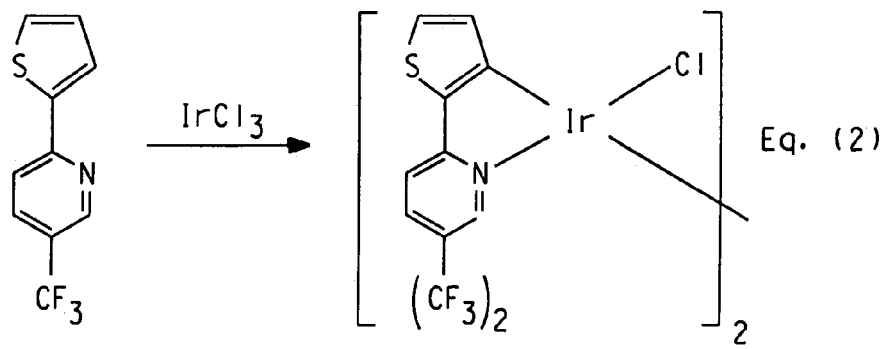

A more preferred precursor iridium complex is an iridium dimer with the L type ligand. The dimer can be the dichloro bridged dimer having Formula XXXIII, shown in FIG. 11, or the dihydroxo bridged dimer having Formula XXXIV, shown in FIG. 11, where:

in Formulae XXXIII and XXXIV:
L is the same or different at each occurrence and is selected from Formulae XXIII through XXVII, shown in FIG. 8, and Formulae XXVIII through XXXII, shown in FIG. 9, as defined above, and in Formula XXXIV:
$R^7$=H, $CH_3$, or $C_2H_5$.

The dichloro bridged dimers having Formula XXXIII, can generally be prepared by reacting iridium trichloride hydrate with the HL ligand precursors, in a suitable solvent, such as 2-ethoxyethanol. This is illustrated for a thienyl-pyridine ligand in Equation (2), shown in FIG. 11. The hydroxo bridged dimers having Formula XXXIV, can generally be prepared by reacting iridium trichloride hydrate with the HL ligand precursors, and then adding NaOH. These dicyclometalated complexes can be isolated and (optionally) purified before further reaction.

3. Platinum

Figure 12:
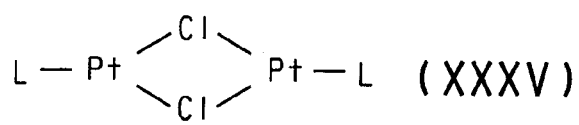
FIG. 12 shows Formula XXXV for a platinum precursor complex; and Equation (3) for preparing a platinum precursor complex.
Figure 12:
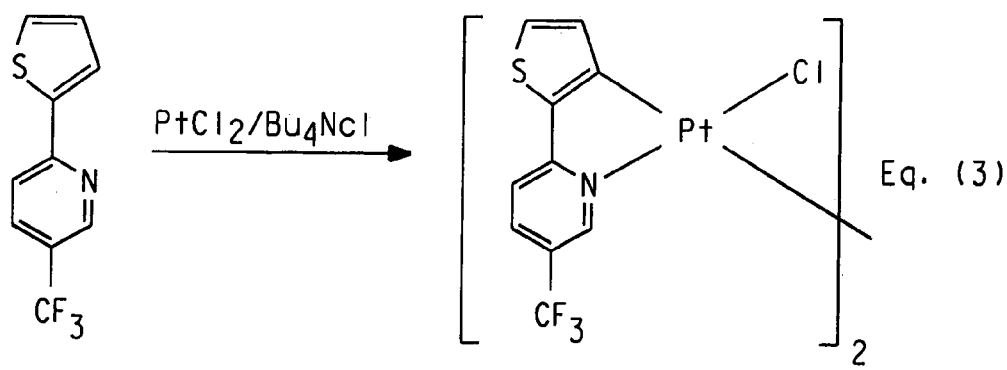

The polymeric-metal complexes with platinum metal are preferably made from precursor platinum compounds which are complexes having at least one ligand, L, which is selected from Formulae XXIII through XXVII, shown in FIG. 8, and from Formulae XXVIII through XXXXII, shown in FIG. 9, as described above. The preferred precursor platinum complex is a platinum dichloro bridged dimer with the L type ligand, having Formula XXXV, shown in FIG. 12, where each L can be the same or different. The dichloro bridged dimers having Formula XXXV, can generally be prepared by reacting platinum dichloride with the HL ligand precursors, in a suitable solvent, such as chlorobenzene or 2-ethoxyethanol, in the presence of an ammonium chloride salt, such as tetrabutylammonium chloride. This is illustrated with a thienyl-pyridine ligand in Equation (3), shown in FIG. 12. The bridged dichloro complexes can be isolated and (optionally) purified before further reaction.

4. Aluminum

Figure 13:
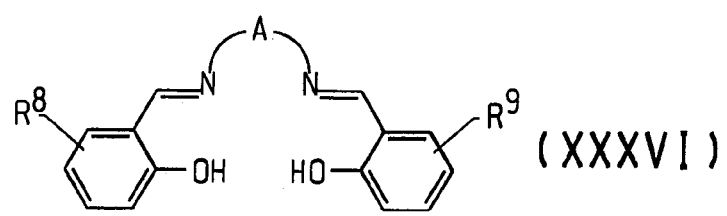
FIG. 13 shows Formula XXXVI for a ligand useful in the invention.

Preferred precursor aluminum compounds are complexes including a multidentate Schiff base ligand. Schiff bases are compounds that are prepared by a condensation reaction between an aldehyde or ketone derivative and a primary amine. By choosing various different poly-amines and aldehydes or ketones, it is possible to generate a wide array of multidentate anionic ligands. A preferred class of Schiff base ligands Formula XXXVI shown in FIG. 13, where $A^1$ represents a bridging group derived from the poly-amine reactant, which can be alkyl, cycloalkyl, or aryl; $R^8$ and $R^9$ represent substituents on the phenyl group of the salicylaldehyde reactant, which can be alkyl or aryl groups. Examples of suitable Schiff base ligands are given in Table 1 below.

TABLE 1

| Ligand | $A^1$ | $R^8$ | $R^9$ |
|---|---|---|---|
| 1-a | 1,2-phenyl | 3, 5-di-t-butyl | 3, 5-di-t-butyl |
| 1-b | Cis-1,2-cyclohexyl | 3, 5-di-t-butyl | 3, 5-di-t-butyl |
| 1-c | Trans-1,2-cyclohexyl | 3, 5-di-t-butyl | 3, 5-di-t-butyl |

One useful precursor aluminum complex can be made by the addition of one molar equivalent of triethylaluminum to the Schiff base compound in hexane or toluene solvent. This forms the ethyl aluminum Schiff base complex.

III. Polymeric-Metal Complexes

The polymeric-metal complexes are generally prepared by adding a precursor metal compound to a functionalized polymer to which it will coordinate. The specific choice of functionalized polymer is dependent on the nature of the precursor metal compound to be added. More than one type of metal can be coordinated to a single functionalized polymer.

A general means of attachment of a metal-ligand precursor complex to a polymeric backbone involves two different approaches. Both require the use of a polymer derivative that contains a Lewis base functionality (X) appended to the primary polymer chain (backbone). This functionality can be (Method A, shown below) the first-type functional group which coordinates directly to the metal, thus making it a ligand in the metal primary coordination sphere (with additional ligands, $L_n$). Alternatively, (Method B, shown below) the polymer functionality can be attached covalently at a proximal site on a ligand (L') that is a component of the primary coordination sphere (with additional ligands, $L_n$).

Method A

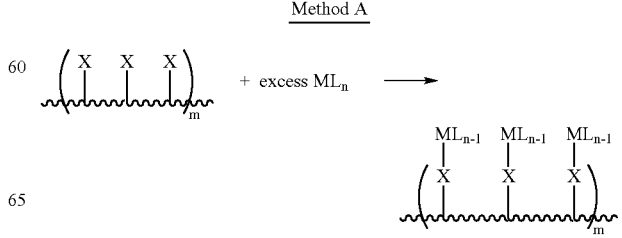

-continued

Method B

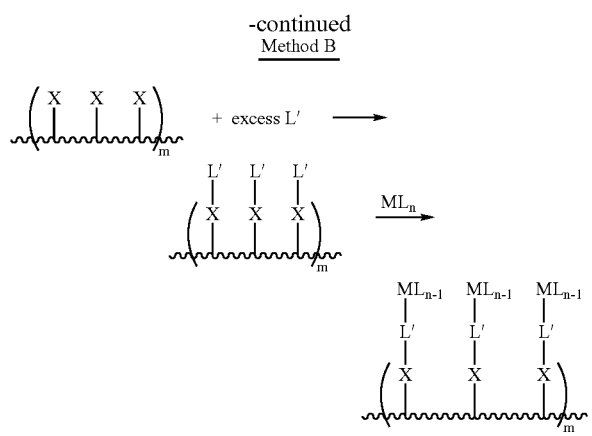

Either method may be used to append any metal-to-ligand charge transfer (MLCT) emitters (including Re-, Ru-, and Os-diimine and Rh-, Ir-, Pd-, and Pt-phenylpyridyl complexes), any intraligand charge transfer emitter complexes (including Al and Zn Schiff base complexes), or any lanthanide (atomic) emitter complexes (including Eu acetylacetonate complexes). For example, the polymer-bound Lewis base could either be directly attached to the metal or be attached via an acceptor functionality appended from a bipyridyl or phenylpyridyl ligand.

This can be illustrated more specifically with the class of $[Re(CO)_3(2,2'\text{-bipyridyl})L]$ emitters. A polymer-bound arylsulfonate functionality can be directly coordinated to Re using Method A. Alternatively, Method B can be used to condense a polymer-bound hydroxyethyl functionality with a 2,2'-bipyridyl derivative that has a carboxylic acid functionality appended from a pyridyl carbon atom. The exact reaction conditions vary with the specific materials used. In general, moderate heat is applied, such as refluxing in a solvent with a boiling point of 100° C. or less. The reaction products can then be recovered by standard solvent removal and purification procedures.

The polymeric lanthanide complexes can generally be prepared by the addition of simple metal salts, such as the halide or acetate salts, to polymers having β-dicarbonyl functional groups in the presence of the other phosphine oxide, N-oxide, or diimine ligands. Solvents such as methylene chloride can be used. Alternatively, complexes of the lanthanides with β-dicarbonyls can be added to polymers having diimine functional groups, such as phenanthroline or bipyridine; phosphine oxide functional groups; or N-oxide functional groups.

Figure 14:
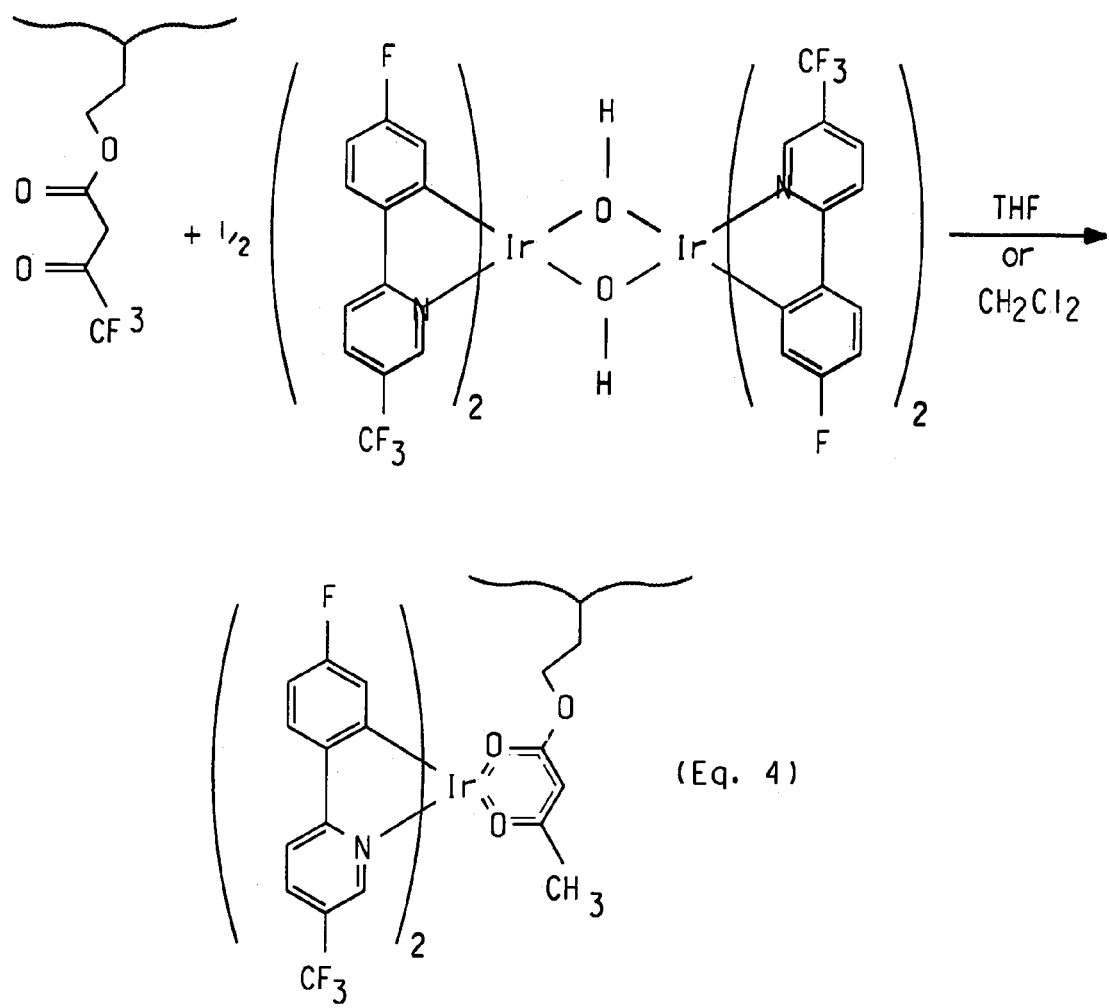
FIG. 14 shows Equation (4) for forming a polymeric metal complex with iridium.

The polymeric iridium and platinum complexes are most conveniently prepared from the precursor metal dimers, Formulae XII, XIV, or XV, and polymers with β-dicarbonyl functionality. This is illustrated for an iridium complex in Equation (4) shown in FIG. 14. The reaction rate is very dependent upon the nature of the solvent. In THF it requires several days; in dichloromethane, several hours.

Figure 15:
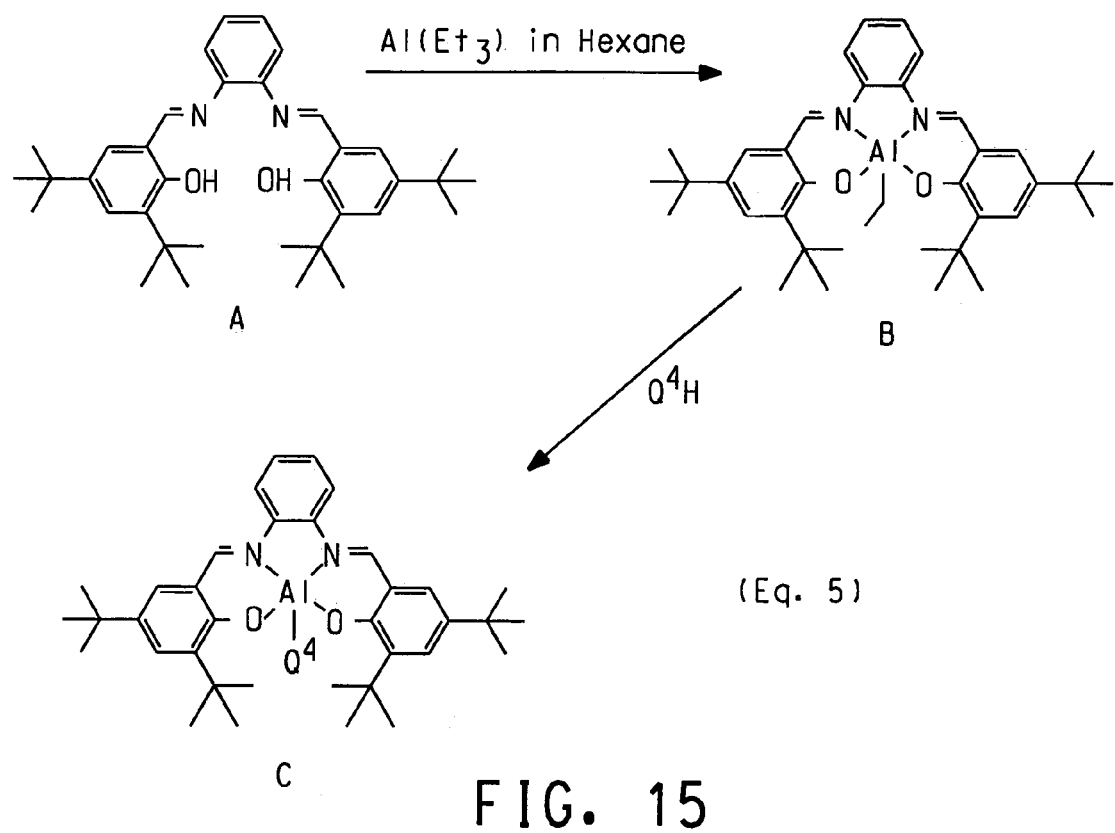
FIG. 15 shows Equation (5) for forming a polymeric metal complex with aluminum.

The polymeric aluminum complexes are conveniently prepared from the ethyl aluminum Schiff base precursor complex and an acidic functionalized polymer. This is illustrated in the reaction scheme shown as Equation (5) in FIG. 15.

In this reaction scheme, $Q^4H$ represents the polymer functionalized with a carboxylic acid or sulfonic acid group. As the ethyl complex reacts with the acid functionality, ethane is evolved and the conjugate base of the polymeric acid ($Q^4$) becomes bonded to the aluminum.

The polymeric metal complexes of the invention can generally be coated from conventional solvents. The solvent used will depend on the nature of the polymeric backbone. For polyfluorene backbones, solvents such as tetrahydrofuran, toluene, chlorobenzene, chloroform, and methylene chloride, can be used.

In one embodiment, preferred polymeric backbones are polyfluorenes. Copolymers of fluorene type monomers can generally be prepared by three known synthetic routes. In the first synthetic method, as described in Yamamoto, Progress in Polymer Science, Vol. 17, p 1153 (1992), the dihalo, preferably dibromo, derivatives of the monomeric units are reacted with a stoichiometric amount of a zerovalent nickel compound, such as bis(1,5-cyclooctadiene)nickel (0). In the second method, as described in Colon et al., Journal of Polymer Science, Part A, Polymer chemistry Edition, Vol. 28, p. 367 (1990), The dihalo, preferably dibromo, derivatives of the monomeric units are reacted with catalytic amounts of Ni(II) compounds in the presence of stoichiometric amounts of a material capable of reducing the divalent nickel ion to zerovalent nickel. Suitable materials include zinc, magnesium, calcium and lithium. In the third synthetic method, as described in U.S. Pat. No. 5,962, 631, and published PCT application WO 00/53565, a dihalo derivative of one monomeric unit is reacted with a derivative of another monomeric unit having two reactive groups selected from boronic acid, boronic acid esters, and boranes, in the presence of a zerovalent palladium catalyst, such as tetrakis(triphenylphosphine)Pd. This third reaction can take place in a two-phase medium.

Preferred metals are Ir and Pt, having one or more ligands selected from Formulae XXIII through XXXII.

V. Luminescent Materials

The polymeric metal complex of the invention is useful as a luminescent material, because, the charge transport and processing properties of conjugated polymers are combined with the luminescent efficiency and color of metal complex emitters.

The luminescent material of the invention contains at least one polymeric metal complex composition described above. The luminescent material may exhibit photoluminescence, where the luminescence results from the application of visible, infrared, or ultraviolet radiation, usually ultraviolet. Alternatively, the luminescent material may exhibit electroluminescense, where the luminescence results from the application of an electric field. In yet another embodiment, the luminescent material may exhibit both electroluminescence and photoluminescence.

In the polymeric metal complexes of the invention, the electronic properties of the metal complex moiety are not coupled with the conjugated polymeric backbone because of the first-type inert spacer group. The luminescent properties of the polymeric metal complex are therefore primarily governed by the choice of the metal and the coordinated ligands. In the polymeric metal complex, it is preferred that from about 0.1% to about 20% of the monomeric units have a metal attached; more preferably about 0.5–10%. It is possible to combine more than one type of metal precursor complex with a functionalized polymer resulting in emission of more than one color. However, it is preferred to combine a single type of metal precursor complex with the functionalized polymer.

VI. Electronic Devices

Electronic devices of the present invention are useful to exhibit photoluminescent and/or electroluminescent properties. They can be used in light-emitting diodes, which are discussed further below, photodiodes, photodetectors, as photoconductors, as in xerographic applications, and in illumination devices.

Figure 16:
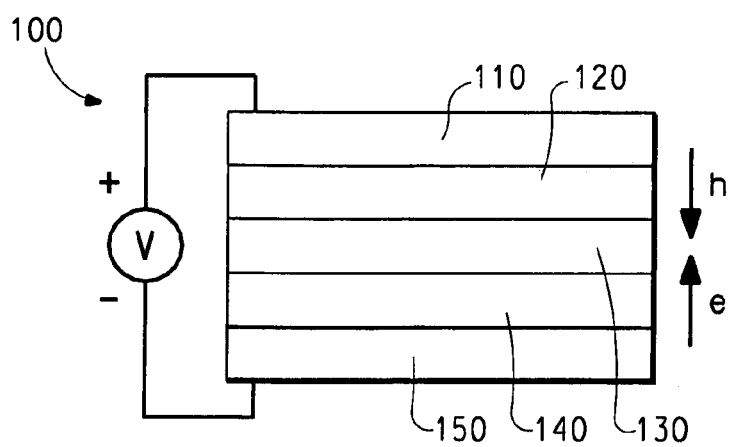
FIG. 16 is a schematic diagram of a light-emitting diode (LED).

Light-emitting diodes are referred to as LEDs or, when the active material is organic, as OLEDs. As stated above, OLEDs generally have a structure in which an organic active layer is sandwiched between two electrical contact layers. OLEDs frequently have additional hole transport and electron transport layers. A typical structure is shown in FIG. 16. The device 100 has an anode layer 110 and a cathode layer 150. Adjacent to the anode is an optional layer 120 comprising hole transport material. Adjacent to the cathode is an optional layer 140 comprising an electron transport material. Between the anode or hole transport layer and the cathode or electron transport layer is the emitting layer 130. When a voltage is applied as best seen in FIG. 16, the electrons and holes move in the directions indicated by the arrows. The electrons and holes combine in the light-emitting layer to form an excited state, sometimes called an exciton. It is from the excitons that photons 160 are emitted. The exciton can also decay via non-radiative processes. This is known as quenching.

The polymeric metal complexes of the invention are particularly useful as the active material in the emitting layer of an OLED.

Where the emitting layer includes the polymeric metal complex, additional materials can be present in the emitting layer with the polymeric-metal complex. For example, a luminescent dye may be present to alter the color of emission.

The polymeric metal complex may also be useful as a charge transportmaterial. The charge transport materials can be hole transport materials or electron transport materials. Here, hole transport material is defined as material that can receive a positive charge and move it through the thickness of the material with relatively high efficiency and small loss. Electron transport material is defined as material that can receive a negative charge and move it through the thickness of the material with relatively high efficiency and small loss. Some materials can transport both electrons and holes and are more flexible to use.

To achieve high efficiency in the LED, the HOMO (highest occupied molecular orbital) of the hole transport material should align with the work function of the anode, the LUMO (lowest unoccupied molecular orbital) of the electron transport material should align with the work function of the cathode. Chemical compatibility and processibility of the materials are also important considerations in selecting the electron and hole transport materials.

In addition to the polymer metal complex, other suitable charge transport materials include, but are not limited to, for optional layer 120, hole transport materials listed, in Kirk-Othmer Encyclopedia of Chemical Technology, Fourth Edition, Vol. 18, p. 837–860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino) phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl) cyclobutane (DCZB), N,N,N',N'-tetrakis(4-methylphenyl)-(1,1'-biphenyl)-4,4'-diamine (TTB), and porphyrinic compounds, such as copper phthalocyanine. Commonly used hole transporting polymers are polyvinylcarbazole (PVK), (phenylmethyl)polysilane, poly(3,4-ethylened ioxythiophene) (PEDOT), and polyaniline (PANI). It is also possible to obtain hole transporting polymers by doping hole transporting molecules such as those mentioned above into polymers such as polystyrene and polycarbonate.

Other examples of suitable electron transport materials (for optional layer 140) include metal chelated oxinoid compounds, such as tris(8-hydroxyquinolato)aluminum ($Alq_3$); phenanthroline-based compounds, such as 2,9-dimethyl-4,7-diphenyl-1,10-phenanthroline (DDPA) or 4,7-diphenyl-1,10-phenanthroline (DPA); and azole compounds such as 2-(4-biphenylyl)-5-(4-t-butylphenyl)-1,3,4-oxadiazole (PBD), 4,4'-N,N'-dicarbazole biphenyl (BCP), and 3-(4-biphenylyl)-4-phenyl-5-(4-t-butylphenyl)-1,2,4-triazole (TAZ). Layer 140 can function both to facilitate electron transport, and also serve as a buffer layer or confinement layer to prevent quenching of the exciton at layer interfaces. Preferably, this layer promotes electron mobility and reduces exciton quenching.

The other layers in the OLED can be selected from any materials that are known to be useful in such layers. The anode 110, is an electrode that is particularly efficient for injecting positive charge carriers. It can be made of, for example materials containing a metal, mixed metal, alloy, metal oxide or mixed-metal oxide, or it can be a conducting polymer. Suitable metals include the Group 11 metals, the metals in Groups 4, 5, and 6, and the Groups 8–10 transition metals, as shown on the periodic table of elements (current IUPAC format). If the anode is to be light-transmitting, mixed-metal oxides of Groups 2, 3, 4, 13 and 14 metals, such as indium-tin-oxide, or a conducting polymer, such as polyaniline, can be used. At least one of the anode and cathode should be at least partially transparent to allow the generated light to be observed.

The cathode 150, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, the lanthanides, and the actinides. Materials such as aluminum, indium, calcium, barium, and magnesium, as well as combinations, can be used. Li-containing compounds can also be deposited between the organic layer and the cathode layer to lower the operating voltage.

Although the functional layers 110 through 150 have each been shown as a single layer in FIG. 16, it is possible to have multiple layers of the same or different materials for any or all of these.

The OLED can be prepared by sequentially depositing the individual layers on a suitable substrate. Substrates such as glass and polymeric films can be used. The organic layers can be coated from solutions or dispersions in suitable solvents, using any conventional coating technique. In general, the different layers will have the following range of thicknesses: anode 110, 500–5000 Å, preferably 1000–2000 Å; optional hole transport layer 120, 50–3000 Å, preferably 600–2000 Å; light-emitting layer 130, 10–1000 Å, preferably 100–800 Å; optional electron transport layer 140, 50–1000 Å, preferably 200–800 Å; cathode 150, 200–10000 Å, preferably 300–5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

It is understood that the efficiency of devices made with the polymeric-metal complexes of the invention, can be further improved by optimizing the other layers in the device. For example, more efficient cathodes such as Ca, Ba or Li can be used. Shaped substrates and novel hole transport materials that result in a reduction in operating voltage or increase quantum efficiency are also applicable. Additional layers can also be added to tailor the energy levels of the various layers and facilitate electroluminescence.

EXAMPLES

The following examples illustrate certain features and advantages of the present invention. They are intended to be illustrative of the invention, but not limiting. All percentages are by weight, unless otherwise indicated.

Example 1

Prophetic Example

This example illustrates the formation of a functionalized conjugated polymer.

A fluorene monomer will be prepared by reaction of a dibromofluorene with a bromoalkanol, having a protected alcohol group (—$OX^1$). The alcohol group will be protected by any of the standard techniques know to those skilled in the art. The protecting group $X^1$ can be, for example, a pyranyl ether (-OTHP, where THP is tetrahydropyran) or a silylether (—$OSiR_3$, where R is a bulky alkyl group such as t-butyl or i-propyl).

As shown in Equation 6 below, in a first step, 3,6-dibromo fluorene is reacted with 6-bromohexanol protected with THP under phase transfer conditions using sodium hydroxide base to give a hexyl alcohol derivatized fluorene monomer. In a second step, the initial product will be reacted with excess alkyl iodide, also under phase transfer conditions.

Equation 6

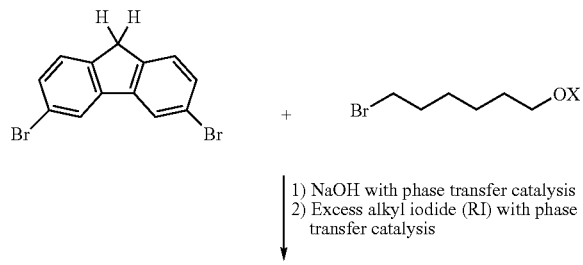

1) NaOH with phase transfer catalysis
2) Excess alkyl iodide (RI) with phase transfer catalysis -continued

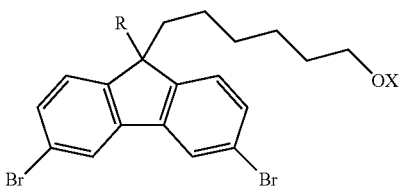

where R is an alkyl group having from 1 to 12 carbon atoms.

This monomer will then be polymerized under standard conditions with bis-9-(2-ethylhexyl)-dibromofluorene in a mole ratio of 1:9.

Under inert conditions, DMF (5 ml) will be added to a 50 ml Schlenck tube equipped with a stirring bar and containing bis(1,5-cyclooctadiene)nickel(0) (5 mmol), 2,2'-bipyridyl (5 mmol), and 1,5-cyclooctadiene (5 mmol). The ensuing deep blue/purple solution will be stirred at 60° C. for 30 minutes, and then a solution of the hexyl alcohol derivatized fluorene monomer prepared above (0.25 mmol) and bis-9-(2-ethyl-hexyl)-dibromofluorene (2.25 mmol) in toluene (20 ml) will be added via syringe. The reaction mixture then will be stirred at 75° C. for 1 day. The mixture will be cooled to room temperature and precipitated into a solution of methanol (100 ml), acetone (100 ml) and concentrated hydrochloric acid (5 ml). The alcohol protecting group will be removed by reaction with the acid. After stirring for 2 hours, the mixture will be filtered. The solid residue will be then dissolved in chloroform, and again precipitated into a solution of methanol (100 ml), acetone (100 ml) and concentrated hydrochloric acid (5 ml). After stirring for 1 hour, the mixture will be filtered. Finally the residue will be successively washed with methanol, water and methanol and dried in vacuo. The resulting polymer containing 10% of repeat units bearing the hexyl alcohol functionality then will be isolated and transesterified by reaction with excess ethylacetoacetate under acidic conditions—distilling out ethanol. The final isolated polymer at this stage will have the general representation as shown in Formula XXXVII below:

Formula XXXVII

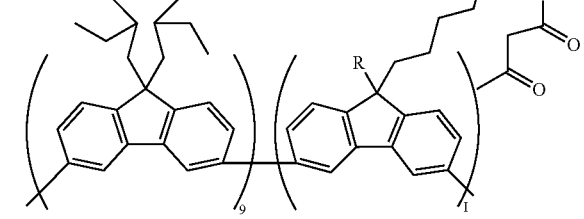

Example 2

This example illustrates the preparation of the hydroxo dimer, [IrOH{2-(2,4-difluoro-phenyl)-isoquinoline}$_2$]$_2$, as a precursor iridium complex.

1-(2,4-difluoro-phenyl)-isoquinoline:

2,4-difluorophenylboronic acid (Aldrich Chemical Co., 13.8 g, 87.4 mmol), 1-chloroisoquinoline (Adrich Chemical Co., 13 g, 79.4 mmol), tetrakistriphenylphosphine palladium (0) (Aldrich, 3.00 g, 2.59 mmol), potassium carbonate (EM Science, 24.2 g, 175 mmol), water (300 mL), and dimethoxyethane (Aldrich, 300 mL) were allowed to stir at reflux for 20 h under N$_2$, after which time the mixture was cooled to room temperature and the organic and aqueous layers were separated. The aqueous layer was extracted with 3×150 mL of diethyl ether, and the combined organic fractions were dried with sodium sulfate, filtered, and the filtrate was evaporated to dryness. The crude material was chromatographed on a silica gel column, first by eluting the catalyst byproduct with 4:1 hexanes/CH$_2$Cl$_2$, and finally the product was eluted with CH$_2$Cl$_2$/MeOH (9.5:0.5, product R$_f$=0.7). The pure product fractions were collected and dried in vacuo, to afford 17.7 g (92% isolated yield) of a light yellow solid, >95% pure NMR spectroscopy. $^1$H NMR (CDCl$_3$, 296 K, 300 MHz): δ 8.61 (1H, d, J=5.7 Hz), 7.89 (1H, d, J=8.2 Hz), 7.67–7.85 (3H, m), 7.52–7.63 (2H, m), 6.95–7.12 (2H, m) ppm. $^{19}$F NMR (CDCl$_3$, 296K, 282 MHz) δ –109.01 (1F, brs), –109.87 (1F, d, J$_{F-F}$=8.5 Hz).

[IrOH{1-(2,4-difluoro-phenyl)-isoquinoline}$_2$]$_2$:

A mixture of IrCl$_3$.nH$_2$O (54% Ir; 500 mg), 1-(2,4-difluoro-phenyl)-isoquinoline, from above, (800 mg), water (5 mL), and 2-ethoxyethanol (20 mL) will be vigorously stirred under reflux for 4.5 hours. After a solution of NaOH (2.3 g) in water (5 mL) will be added, followed by 20 mL of water, the mixture will be stirred under reflux for 2 hours. The mixture will be cooled down to room temperature, diluted with 50 mL of water, and filtered. The solid will be vigorously stirred under reflux with 30 mL of 1,2-dichloroethane and aqueous NaOH (2.2 g in 8 mL of water) for 6 hours. The organic solvent will be evaporated from the mixture to leave a suspension of a red solid in the aqueous phase. The red solid will be separated by filtration, thoroughly washed with water, and dried under vacuum to produce the iridium hydroxo dimer.

Example 3

Prophetic Example

As shown in Equation 7 below, one half of an equivalent (per functional group of the conjugated polymer) of the iridium hydroxo dimer precursor complex from Example 2 will be dissolved in THF containing the conjugated functionalized polymer from Example 1. Excess sodium carbonate will be added and the mixture stirred and warmed for 24 hours under nitrogen. The solution will be cooled and solvent evaporated to leave a solid residue, which will be extracted extensively with methylene chloride. This solution will be then evaporated and dried to yield the desired Ir functionalized polymeric material which will be a red emitter.

Equation 7

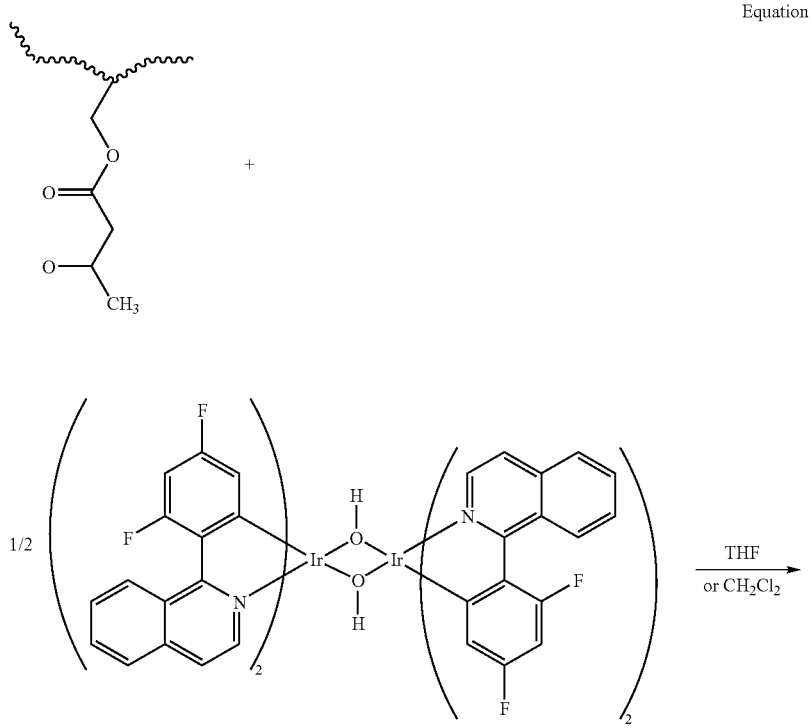

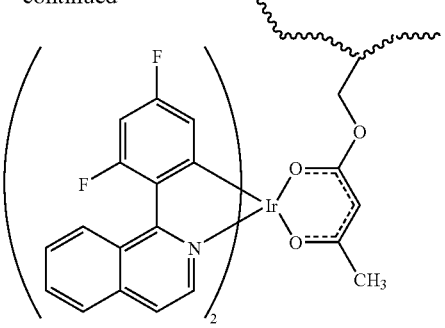

Example 4

This example illustrates the preparation of a platinum precursor complex, shown in Formula XXXVIII below:

Formula XXXVIII

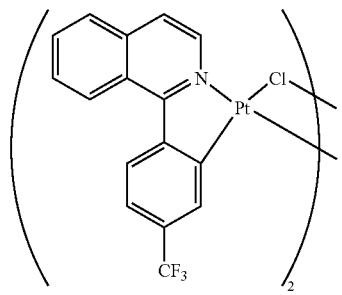

1-(4-trifluoromethyl-phenyl)-isoguinoline:

This was made according to the procedure described in Example 2, using 4-trifluoromethylphenylboronic acid.

[PtCl{2-(4-trifluoromethylphenyl)-isoguinoline}]$_2$:

2-(4-Trifluoromethylphenyl)-isoquinoline from above (6.8 mmol), platinum(II) chloride (Strem Chemicals, 6.2 mmol), anhydrous tetrabutylammonium chloride (Aldrich Chemical Co., 171 mg, 0.62 mmol), and chlorobenzene (Aldrich) will be allowed to reflux under nitrogen for 15 hours, after which time the resulting precipitated product will be isolated by filtration, washed with methanol, and dried in vacuo, to afford the desired product as an off-white solid.

Example 5

Prophetic Example

One half of an equivalent (per functional group of the conjugated polymer) of the platinum dichloro dimer precursor complex from Example 4 will be dissolved in 1:5 mixture of 2-ethoxyethanol:o-dichlorobenzene containing the conjugated functionalized polymer from Example 1. Excess sodium carbonate will be added and the mixture stirred and heated to reflux for 24 hours under nitrogen. The solution will be cooled and solvent evaporated to leave a solid residue, which will be extracted extensively with methylene chloride. This solution then will be evaporated and dried to yield the desired Pt functionalized polymeric material which will be a red emitter.

Example 6

Prophetic Example

This example illustrates the formation of thin film OLED devices.

A substrate of indium tin oxide (ITO) on glass will be used, having an ITO thickness of about 1000 to 1500 Å. The HT layer will be spin-coated onto the ITO substrate. The HT layer will be PEDOT (Baytron® P from Bayer, Germany) at a thickness of 2000 Å. The polymeric metal complex (200 mg) will be dissolved in 10 mL toluene (0.5–2.0% w/v), filtered through a 0.45 micron filter, and spin-coated to a thickness of 500–1000 Å. For the cathode, Ba and Al layers will be vapor deposited on top of the EL layers under a vacuum of $1 \times 10^{-6}$ torr. The final thickness of the Ba layer will be 30 Å; the thickness of the Al layer will be 3000 Å. Device performance will be tested inside a dry box using a calibrated Si photodiode.

Example 7

This example illustrates the preparation of the hydroxo dimer. [IrOH{1-(4-tert-butyl-phenyl)-isoquinoline}$_2$]$_2$, as a precursor iridium complex.

1-(4-tert-butylphenyl)-isoguinoline:

4-tert-butylphenylboronic acid (Aldrich Chemical Co., 5.00 g, 30.56 mmmol), 1-chloroisoquinoline (Adrich Chemical Co., 5.44 g, 30.56 mmol), tetrakistriphenylphosphine palladium(0) (Aldrich, 800 mg, 0.69 mmol), potassium carbonate (EM Science, 12.5 g, 23.4 mmol), water (50 mL), and dimethoxyethane (Aldrich, 75 mL) were allowed to stir at reflux for 20 h under N$_2$, after which time the mixture was cooled to room temperature and the organic and aqueous layers were separated. The aqueous layer was extracted with 3×75 mL of diethyl ether, and the combined organic fractions were dried with sodium sulfate, filtered, and the filtrate was evaporated to dryness. The crude material was chromatographed on a silica gel column, first by eluting the catalyst byproduct with 4:1 hexanes/dichloromethane, and finally the product was eluted with dichloromethane/MeOH (9.5:0.5, product R$_f$=0.7). The pure product fractions were collected and dried in vacuo, to afford 4.5 g (56% isolated yield) of a light yellow solid, >95% pure NMR spectroscopy. $^1$H NMR (CDCl$_3$, 296 K, 300 MHz): δ=8.58 (1H, d, J=5.70 Hz), 8.15 (1H, d, J=8.5 Hz), 7.83 (1H, d, J=8.5 Hz), 7.5–7.7 (7H, m), 1.38 (9H, s) ppm.

IrCl{1-(4-t-Bu-phenyl)-isoquinoline}₂]₂:

1-(4-t-Bu-phenyl)-isoquinoline from above (1.00 g, 3.82 mmol), IrCl₃(H₂O)₃ (Strem Chemicals, 633 mg, 1.79 mmol), and 2-ethoxyethanol (Aldrich Chemical Co., 40 mL) were allowed to stir at reflux for 15 h, after which time the mixture was poured into an equal volume of water. The resulting orange precipitate was isolated by filtration, washed with water, and allowed to dry in vacuo. Then the solid was re-dissolved in dichloromethane and passed through a silica gel pad. The red eluted dichloromethane solution was evaporated to dryness, and the resulting solid was suspended in hexanes. The solid was isolated by filtration to afford 650 mg (49%) of a red-orange solid, >95% pure by NMR spectroscopy. $^1$H NMR (CD₂Cl₂, 296 K, 300 MHz): δ=9.37 (4H, d, J=6.5 Hz), 8.95 (4H, d, J=8.2 Hz), 8.07 (4H, d, J=8.5 Hz), 7.90 (4H, dd, J=1.4 and 8.2 Hz), 7.7–7.9 (8H, m), 6.94 (4H, dd, J=2.0 and 8.4 Hz), 6.86 (4H, d, J=6.4 Hz), 5.92 (4H, d, J=2.0 Hz), 0.81 (36H, s) ppm.

[IrOH{1-(4-tert-butyl-phenyl)-isoquinoline}₂]₂:

A round-bottom flask was charged with [IrCl{1-(4-tert-butyl-phenyl)-isoquinoline}₂]₂ (2.18 g, 1.46 mmol) from above, NaOH (2.18 g) in water (25 mL), followed by 25 mL of ethoxyethanol. The mixture was stirred under reflux for 2 hours. The resulting brown suspension was cooled down to room temperature, diluted with 100 mL of water and filtered. The solid was vigorously stirred under reflux with 46 mL of 1,2-dichloroethane and aqueous NaOH (2.03 g in 20 mL of water) for 6 hours. The organic solvent was evaporated from the mixture to leave a suspension of a brown solid in the aqueous phase. The solid was separated by filtration, thoroughly washed with water, and dried under vacuum to produce [IrOH{1-(4-tert-butyl-phenyl)-isoquinoline}₂]₂ as a dark-red solid (2.108 g, 99% yield).

Example 8

This example illustrates the formation of a polymer which can be converted to a functionalized polymer.

Comonomers:

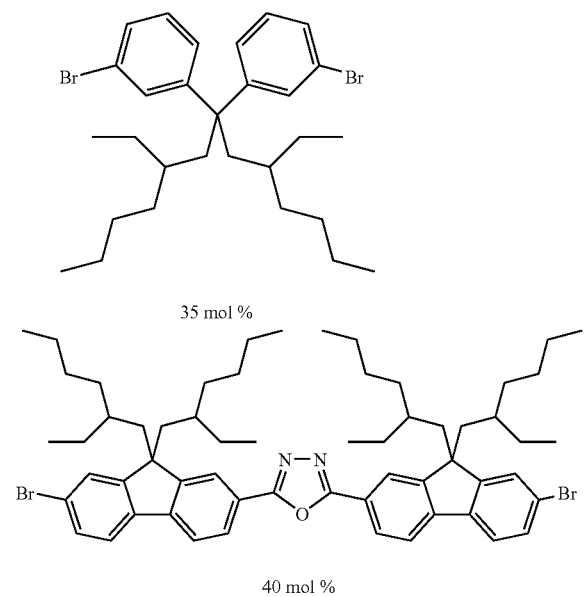

35 mol %

40 mol %

-continued

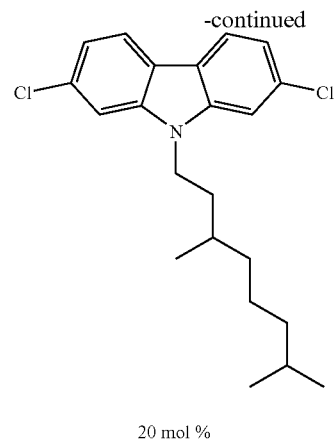

20 mol %

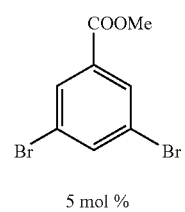

5 mol %

Polymer A:

Under inert conditions, DMF (6 ml) was added to a Schlenck tube equipped with a stirring bar and containing bis(1,5-cyclooctadiene)nickel(0) (1.667 g, 6.06 mmol), 2,2'-bipyridyl (0.947 g, 6.06 mmol), and 1,5-cyclooctadiene (0.656 g, 6.06 mmol). The ensuing deep blue/purple solution was stirred at 60° C. for 30 minutes, and then a solution of a first monomer, 2,7-dibromo-9,9-bis-(2-ethyl-hexyl)-9H-fluorene (0.576 g, 1.05 mmol), a second monomer, 2,5-bis-[7-bromo-9,9-bis-(2-ethyl-hexyl)-9H-fluoren-2-yl]-[1,3,4] oxadiazole (1.206 g, 1.20 mmol) a third monomer, 2,7-dichloro-9-(3,7-dimethyl-octyl)-9H-carbazole (0.217 g, 0.60 mmol) and a forth monomer, 3,5-dibromo-benzoic acid methyl ester (0.044 g, 0.15 mmol) in toluene (25 ml) was added via syringe. The reaction mixture was then stirred at 75° C. for 24 h. The mixture was cooled to room temperature and precipitated into a solution of methanol (100 ml), acetone (100 ml) and concentrated hydrochloric acid (5 ml). After stirring for 2 hours, the mixture was filtered. The solid residue was then dissolved in chloroform, and again precipitated into a solution of methanol (100 ml), acetone (100 ml) and concentrated hydrochloric acid (5 ml). After stirring for 1 hour, the mixture was filtered. The solid was again dissolved in chloroform and precipitated in pure methanol. Finally the residue was successively washed with methanol, water and methanol and dried in vacuo.

Example 9

This example illustrates the formation of a polymeric metal complex of the invention.

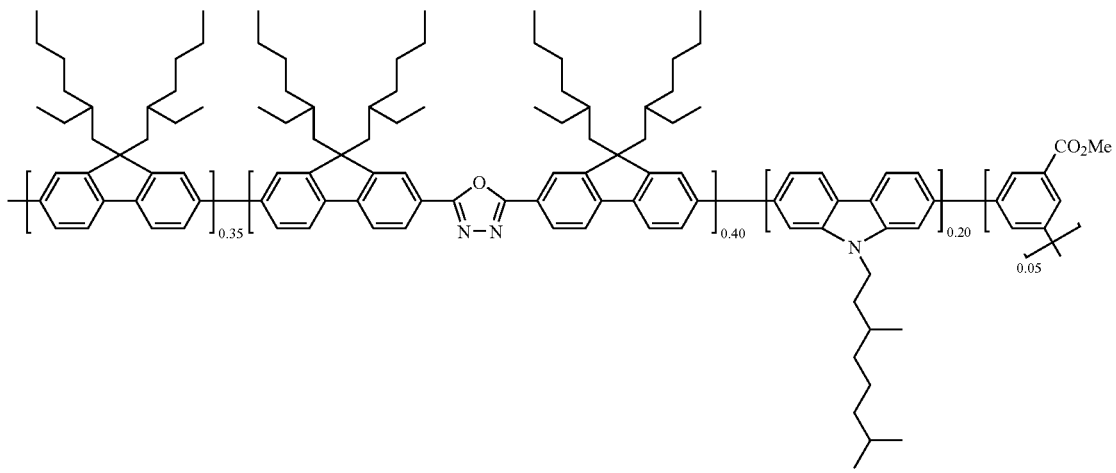

Polymer A

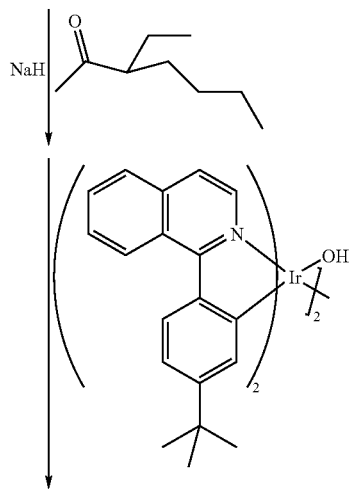

Polymeric Metal Complex

Sodium hydride (0.002 g, 0.08 mmol) was suspended in anhydrous THF (50 mL), followed by addition of Polymer A from Example 8 (0.250 g, containing 0.023 mmol of ester functionality) and 3-ethyl-heptan-2-one (0.5 mL). The reaction was then allowed to reflux under nitrogen for 96 h. The resulting viscous orange mixture was cooled to room temperature, quenched with 10 mL $H_2O$ and extracted in $CHCl_3$ (2×20 mL). The volatiles were evaporated to give a yellow solid, which was dissolved in $CHCl_3$ (50 mL) and $H_2O$ (25 mL). The $H_2O$ layer was neutralized with 1% HCl and then the layers were separated. The organic layer was washed with 10% $NaHCO_3$ (2×20 mL) and evaporated to dryness. The resulting functionalized polymer, which was an acetylacetonate-containing polymer, was purified by precipitation from MeOH/acetone (50/50, 100 mL) to give a pale-yellow solid (0.238 g). Anal. Calcd: C, 86.33; H, 9.65; N, 2.56. Found: C, 83.15; H, 9.29; N, 2.46.

The above acetylacetonate-containing polymer (0.150 g) and [IrOH{1-(4-tert-butyl-phenyl)-isoquinoline}$_2$]$_2$ from Example 7 (0.010 g, 0.007 mmol) were placed in a 100 mL round-bottom flask under nitrogen. Dry THF (45 mL) was added and the mixture was refluxed for 24 h. The resulting dark-red solution was diluted with THF (100 mL) and filtered through silica. The evaporation of the solvent yielded a red solid (0.135 g). Anal. Calcd: C, 84.98; H, 9.36; N, 2.64; Ir, 1.65. Found: C, 82.81; H, 8.99; N, 2.59; Ir, 1.88.

What is claimed is:

1. A polymeric metal complex composition comprising (a) a conjugated polymeric backbone; (b) a plurality of a first-type functional groups; and (c) a plurality of first-type inert spacer groups, wherein:
   each of the plurality of first-type functional groups is covalently bound to at least one of the plurality of first-type inert spacer groups, which first-type inert spacer groups are covalently bound to the polymeric backbone; and
   at least a portion of each of the plurality of first-type functional groups is coordinated to at least one metal, wherein at least one of the plurality of first-type inert spacer groups is an alkyl chain of from 4 to 12 carbon atoms.

2. The composition of claim 1, further comprising (d) a plurality of second-type functional groups.

3. The composition of claim 2, wherein at least one of the plurality of second-type functional groups is covalent bound to at least one of a plurality of second-type inert spacer groups, which second-type inert spacer groups are covalently bound to the polymeric backbone.

4. The composition of claim 3, wherein at least one of the plurality of the first-type inert spacer groups is the same composition as at least one of the plurality of the second-type inert spacer groups.

5. The composition of claim 4, wherein at least one of the plurality of first-type functional groups is covalently bound to an inert spacer group that is also covalently bound to at least one of the second-type functional groups.

6. The composition of claim 1, wherein the ratio of the number of first-type inert spacer groups to the number of first-type functional groups is 1:1.

7. The composition of claim 3, wherein the ratio of the number of second-type inert spacer groups to the number of second-type functional groups is 1:1.

8. The composition of claim 1, wherein the conjugated polymeric backbone has at least one recurring monomeric unit selected from fluorenediyls, phenylenes, phenylenevinylenes, oxadiazolediyls, thiophenediyls, and arylaminediyls.

9. The composition of claim 1, wherein the conjugated polymeric backbone has a non-conjugated segment comprising recurring monomeric units selected from vinyl carbazolediyls and triarylmethanediyls.

10. The composition of claim 3, wherein at least one of the plurality of second-type inert spacer groups is an alkyl chain of from 1 to 12 carbon atoms.

11. The composition of claim 1, wherein at least one of the plurality of first type functional groups is selected from β-dicarbonyls, phosphinoalkanols, aminocarboxylic acids, iminocarboxylicacids, salycylic acids, and hydroxyquinolines.

12. The composition of claim 1, wherein at least one of the metals is selected from Iridium, platinum, rhenium and ruthenium.

13. The composition of claim 12, wherein at least one of the metals is further coordinated to at least one ligand selected from 2-arylpyridines, 2-arylpyrimidines and 2-arylquinolines, 2-thienylpyridines, 2-thienylquinolines, 2-thienyldiazines, 2-pyrrolylpyridines, 2-pyrrolyiquinolines, and 2-pyrrolyldiazines.

14. A luminescent material comprising at least one polymeric metal complex composition comprising (a) a conjugated polymeric backbone; (b) a plurality of a first-type functional groups; and (c) a plurality of first-type inert spacer groups, wherein:

each of the plurality of first-type functional groups is covalently bound to at least one of the plurality of first-type inert spacer groups, which first-type inert spacer group is covalently bound to the polymeric backbone, and at least a portion of each of the plurality of first-type functional groups are coordinated to at least one metal, wherein at least one of the plurality of first-type inert spacer groups is an alkyl chain of from 4 to 12 carbon atoms.

15. The luminescent material of claim 14, wherein the at least one polymeric metal complex composition further comprises (d) a plurality of second-type functional groups.

16. The luminescent material of claim 15, wherein at least one of the plurality of second-type functional groups is covalent bound to at least one of a plurality of second-type inert spacer groups, which second-type inert spacer groups are covalently bound to the polymeric backbone.

17. The luminescent material of claim 16, wherein at least one of the plurality of the first-type inert spacer groups is the same composition as at least one of the plurality of the second-type inert spacer groups.

18. The luminescent material of claim 16, wherein at least one of the first-type functional groups is covalently bound to an inert spacer group that is also covalently bound to at least one of the second-type functional groups.

19. The luminescent material of claim 14, wherein the ratio of the number plurality of first-type inert spacer groups to the number of the plurality of first-type functional groups is 1:1.

20. The luminescent material of claim 16, wherein the ratio of the number plurality of second-type inert spacer groups to the number of plurality of second-type functional groups is 1:1.

21. The luminescent material of claim 14 wherein the conjugated polymeric backbone has at feast one recurring monomeric unit selected from fluorenediyls, phenylenes, phenylenevinylenes, oxadiazolediyls, and thiophenediyls.

22. The luminescent material of claim 16 wherein at least one of the plurality of second-type inert spacer groups is an alkyl chain of from 1 to 12 carbon atoms.

23. The luminescent material of claim 14 wherein at least one of the first type functional groups is selected from β-dicarbonyls, phosphinoalkanols, aminocarboxylic acids, iminocarboxylicacids, salycylic acids, and hydroxyquinolines.

24. The luminescent material of claim 14 wherein at least one of the metals is selected from iridium, platinum, rhenium, and ruthenium.

25. The luminescent material of claim 24 wherein at least one of the metals is further coordinated to at least one ligand selected from 2-arylpyridines, 2-arylpyrimidines and 2-arylquinolines, 2-thienylpyridines, 2-thienylquinolines, 2-thienyldiazines, 2-pyrrolylpyridines, 2-pyrrolyiquinolines, and 2-pyrrolyldiazines.

26. The luminescent material of claim 14 wherein the conjugated polymeric backbone has at least one fluorenediyls recurring monomeric unit, the first type functional group is a β-dicarbonyl, and the metal is iridium.

27. An organic electronic device comprising at least one polymeric metal complex composition comprising (a) a conjugated polymeric backbone; (b) a plurality of a first-type functional groups; and (c) a plurality of first-type inert spacer groups, wherein:

each of the plurality of first-type functional groups is covalently bound to at least one of the plurality of first-type inert spacer groups, which first-type inert spacer group is covalently bound to the polymeric backbone, and at least a portion of each of the plurality of first-type functional groups is coordinated to at least one metal, wherein at least one of the plurality of first-type inert spacer groups is an alkyl chain of from 4 to 12 carbon atoms.

28. The device of claim 27, wherein the at least one polymeric metal complex composition further comprises (d) a plurality of second-type functional groups.

29. The device of claim 28, wherein at least one of the plurality of second-type functional groups is covalent bound to at least one of a plurality of second-type inert spacer groups, which second-type inert spacer groups are covalently bound to the polymeric backbone.

30. The device of claim 29, wherein at least one of the plurality of the first-type inert spacer groups is the same composition as at least one of the plurality of the second-type inert spacer groups.

31. The device of claim 30, wherein at least one of the first-type functional groups is covalently bound to an inert spacer group that is also covalently bound to at least one of the second-type functional groups.

32. The device of claim 27, wherein the ratio of the number of plurality of first-type inert spacer groups to the number of plurality of first-type functional groups is 1:1.

33. The device of claim 29, wherein the ratio of the number of plurality of second-type inert spacer groups is covalently bound to the number of plurality of second-type functional groups is 1:1.

34. The device of claim 27 wherein the conjugated polymeric backbone has at least one recurring monomeric unit selected from fluorenediyls, phenylenes, phenylenevinylenes, oxadiazolediyls, and thiophenediyls.

35. The device of claim 29 wherein at least one of the plurality of second-type inert spacer groups is an alkyl chain of from 1 to 12 carbon atoms.

36. The device of claim 27 wherein at least one of the first type functional groups is selected from $\beta$-dicarbonyls, phosphinoalkanols, aminocarboxylic acids, iminocarboxylicacids, salycylic acids, and hydroxyquinolines.

37. The device of claim 27 wherein at least one of the metals is selected from iridium, platinum, rhenium, and ruthenium.

38. The device of claim 37 wherein at least one of the metals is further coordinated to at least one ligand selected from 2-arylpyridines, 2-arylpyrimidines and 2-arylquinolines, 2-thienylpyridines, 2-thienylquinolines, 2-thienyldiazines, 2-pyrrolylpyridines, 2-pyrrolylquinolines, and 2-pyrrolyldiazines.

* * * * *